United States Patent
Needham

(10) Patent No.: US 12,249,407 B2
(45) Date of Patent: Mar. 11, 2025

(54) SYSTEMS AND METHODS OF VALIDATION OF RAPID TEST DEVICE RESULTS WITH ENHANCED IMAGE CAPTURE

(71) Applicant: InBios International, Inc., Seattle, WA (US)

(72) Inventor: James William Needham, Seattle, WA (US)

(73) Assignee: INBIOS INTERNATIONAL, INC., Seattle, WA (US)

( * ) Notice: Subject to any disclaimer, the term of this patent is extended or adjusted under 35 U.S.C. 154(b) by 379 days.

(21) Appl. No.: 17/826,020

(22) Filed: May 26, 2022

(65) Prior Publication Data

US 2023/0386622 A1 Nov. 30, 2023

(51) Int. Cl.
G16H 10/40 (2018.01)
G06T 7/00 (2017.01)
G06T 7/70 (2017.01)

(52) U.S. Cl.
CPC .......... *G16H 10/40* (2018.01); *G06T 7/0012* (2013.01); *G06T 7/70* (2017.01); *G06T 2207/20081* (2013.01); *G06T 2207/20092* (2013.01)

(58) Field of Classification Search
CPC ......... G16H 10/40; G06T 7/70; G06T 7/0012; G06T 2207/20081; G06T 2207/20092
See application file for complete search history.

(56) References Cited

U.S. PATENT DOCUMENTS

| | | | |
|---|---|---|---|
| 9,854,155 B1* | 12/2017 | Sikka | H04N 23/64 |
| 12,014,490 B2* | 6/2024 | Needham | G06T 7/0012 |
| 2012/0063652 A1* | 3/2012 | Chen | G01N 21/274 |
| | | | 382/128 |
| 2016/0148079 A1* | 5/2016 | Shen | G06V 10/454 |
| | | | 382/157 |
| 2017/0085604 A1* | 3/2017 | Morita | H04L 43/0852 |
| 2019/0027251 A1* | 1/2019 | Pulitzer | G16H 30/40 |

\* cited by examiner

*Primary Examiner* — Khai M Nguyen
(74) *Attorney, Agent, or Firm* — Seed IP Law Group LLP

(57) ABSTRACT

Embodiments are directed to use of a rapid-test-validation computing device to determine if a result of a rapid test device is valid and identify the result. The rapid-test-validation computing device captures images of the rapid test device and employs a first artificial intelligence mechanism to determine if the rapid test device is properly aligned in the images. The rapid-test-validation computing device then employs a second artificial intelligence mechanism to determine if a result of the rapid test device is valid or invalid. If the result is valid, the rapid-test-validation computing device employs a third artificial intelligence mechanism to determine and present an objective output of the rapid test device result to a user; otherwise, the rapid-test-validation computing device presents a notification to the user that the rapid test device result is invalid.

24 Claims, 31 Drawing Sheets

FIG. 4A

PATIENT INFORMATION

(*Required)

- First Name:* [First Name]
- Last Name:* [Last Name]
- Email:* [Email]
- Date of Birth:* [MM/DD/YYYY]
- Sex:* [Select ▽]
- Zip code:* [Zip Code]
- State (If in U.S.):* [Select ▽]
- Send results to Health and Human Services ⓘ ◯

[NEXT]

FIG. 3C

< Start Test

Patient Profile Agreement

By creating this patient profile, you must be authorized to provide and share this individual's confidential health data including test results.

This typically includes the elderly, children or others in your care.

You are responsible for ensuring the patient is aware of the Terms of Service prior to providing any information and maintaining appropriate compliance to any regulations while sharing information (e.g., HIPAA).

Federal and local regulations require notifications for all Covid-19 test results (positive and negative). The information requested here and testing results may be shared with the department of Health and Human Services.

[✓ CONFIRM]
[✕ CANCEL]

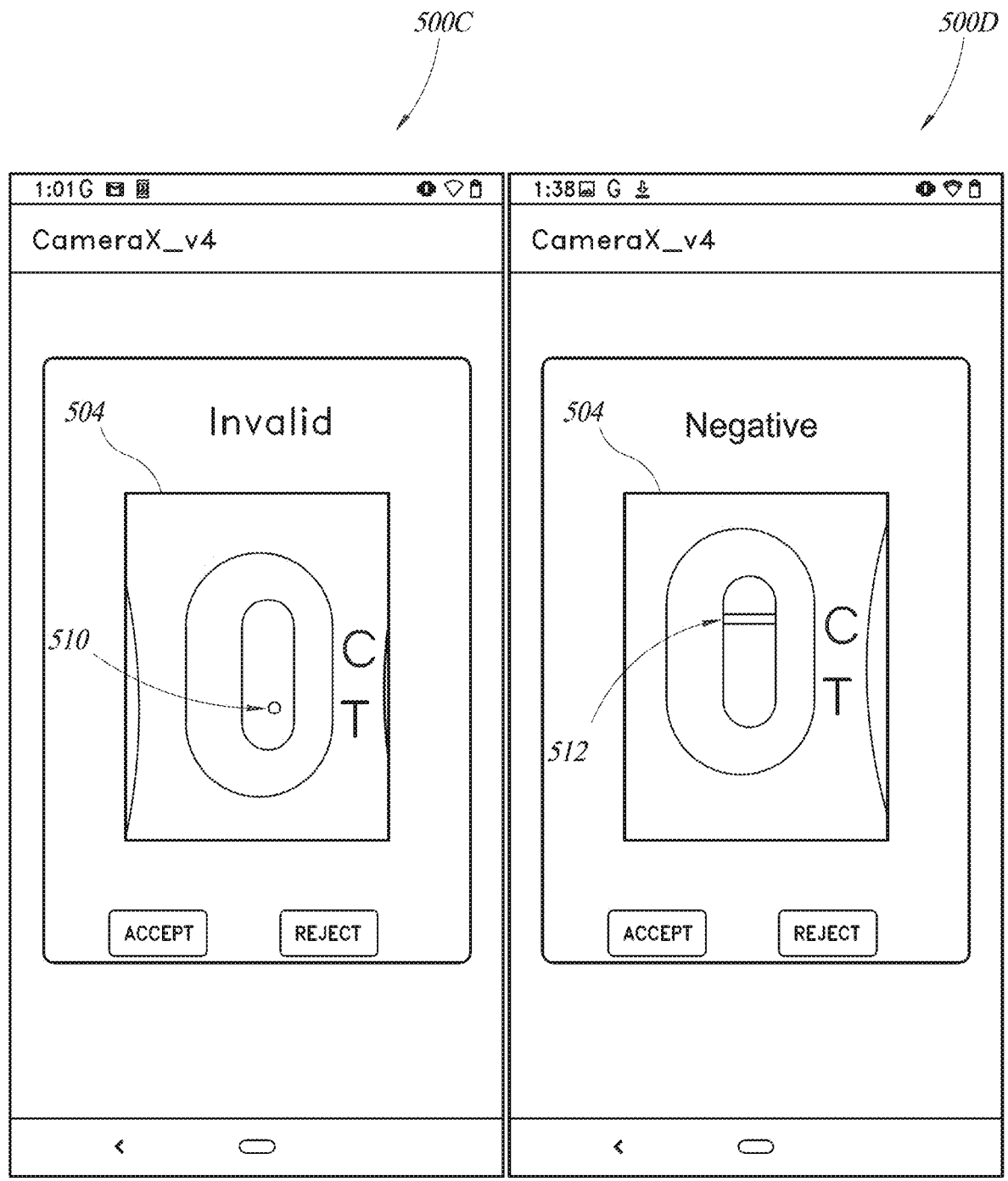
*FIG. 25C*  *FIG. 25D*

SYSTEMS AND METHODS OF VALIDATION OF RAPID TEST DEVICE RESULTS WITH ENHANCED IMAGE CAPTURE

BACKGROUND

Technical Field

The present disclosure relates generally to testing validation, and more particularly to utilizing enhanced image capture to validate and identify rapid test device results.

Description of the Related Art

Medical practitioners often use rapid test devices to determine the presence or absence of a biologically relevant target in a blood or fluid sample. These rapid test devices often output the results via a line, series of dots, or particular color-coded response. For example, a line only at a control location on the rapid test device (and no line at a test location) may indicate the absence of the biologically relevant target in the sample (i.e., a negative test result), whereas as a line at the test location on the rapid test device and a line at the control location may indicate the presence of the biologically relevant target in the sample (i.e., a positive test result). Unfortunately, rapid test device results are often misinterpreted due to subjective interpretations, visual acuity differences and outright operator error. For example, test line signal strengths may be quite weak when the biologically relevant target is present in very low concentrations and the rapid test device may show only a faint test line where proper interpretation may be difficult for naïve operators.

The medical practitioner, however, may view the faint test line as a "negative" test result, which would be an incorrect reading and could cause an inaccurate diagnosis. Moreover, the outputs of some rapid test devices may be color coded with each color representing a different result. Some medical practitioners, however, may not correctly identify the color being displayed depending on how prominent the color is being displayed, the lighting under which the medical practitioner is viewing the rapid test device, vision difficulties of the medical practitioner, or other factors. It is with respect to these and other considerations that the embodiments described herein have been made.

BRIEF SUMMARY

Briefly, and in general terms, a method is disclosed for a rapid test results imaging method. The method includes: capturing one or more first images of a rapid test device using an image capture system with a display screen; presenting the one or more images to a user on the display screen with alignment bars as the one or more first images are being captured; in responsive to determining that the position of the rapid test device relative to the alignment bars is not in an acceptable range and position, prompting the user of the image capture system to reposition the image capture system with respect to the alignment bars; determining, via a tilt detection system of the image capture system, a tilt angle of the image capture system relative to horizontal; in responsive to determining that the tilt angle of the image capture system relative to horizontal is not in an acceptable range, prompting the user of the image capture system to rotate the image capture system relative to horizontal; responsive to the position of the rapid test device being in an acceptable range relative to the alignment bars in at least one of the one or more first images, and responsive to the tilt angle of the image capture system being in an acceptable range relative to horizontal; responsive to the acceptable position and tilt, an optional blur detection method and subsequent trigger of the device autofocus as needed: subsequently capturing one or more second images of the rapid test device; determining if a result of the rapid test device is valid; presenting an invalid-test-result notification to the user if the result of the rapid test device is invalid; determining the qualitative test result of the rapid test device as positive or negative if the rapid test device is valid; determining a quantitative level of the result of the rapid test device if the result of the rapid test device is valid; and presenting the qualitative result and/or the quantitative level of the result to the user.

In some embodiments of the rapid test results imaging method, the tilt detection system uses an accelerometer and an angle sensor in the image capture system. In another aspect of the rapid test results imaging method, the tilt detection system detects a tilt angle along one axis. In still another aspect of the rapid test results imaging method, the tilt detection system detects a tilt angle along multiple axes. In yet another aspect, the rapid test results imaging method further includes displaying a number of degrees for the user to rotate the image capture system.

In one or more embodiments, the rapid test results imaging method further includes: providing a color change on the display screen when the image capture system is rotated from an unacceptable tilt angle relative to horizontal to an acceptable tilt angle relative to horizontal. In another aspect, the rapid test results imaging method further includes: automatically triggering re-autofocus and image capture when the tilt angle is within an acceptable range. In another aspect, the rapid test results imaging method further includes: automatic detections of blur levels in the image and triggering re-autofocus of the device as needed. In still another aspect, the rapid test results imaging method further includes: providing haptic feedback to notify the user that the image capture process started. In still another aspect of the rapid test results imaging method, the tilt detection system determines the tilt angle without use of a marked background of the rapid test device.

In some embodiments, the rapid test results imaging method further comprises exporting, using a scan pass system, a QR code with test results. In another aspect of some embodiments, the rapid test results imaging method further comprises tracking, via multiple timers, concurrent test results. In still another aspect of the rapid test results imaging method, the presenting a quantitative level of the results further includes: presenting an indication of a negative result, low positive result, medium positive result, or strong positive result.

Other embodiments of the disclosure are directed towards a rapid-test-validation computing device. One or more embodiments of this rapid-test-validation computing device include: an image capture system with a display screen; a tilt detection system with an accelerometer and an angle sensor; a memory that stores computer instructions; and a processor that executes the computer instructions to: obtain one or more first images of a rapid test device using the image capture system with a display screen; present the one or more images to a user on the display screen with alignment bars as the one or more first images are being captured; determine a position of the rapid test device in the one or more first images relative to the alignment bars; in responsive to determining that the position of the rapid test device relative to the alignment bars is not in an acceptable range, prompt the user of the image capture system to reposition the image capture system with respect to the alignment bars; determine, via a tilt detection system, a tilt angle of the image capture system with respect to horizontal; in responsive to determining that the tilt angle of the image capture system relative to horizontal is not in an acceptable range, prompt the user of the image capture system to rotate the image capture system relative to horizontal; responsive to the position of the rapid test device being in an acceptable range relative to the alignment bars in at least one of the one or more first images, and responsive to the tilt angle of the image capture system being in an acceptable range relative to horizontal: capture one or more second images of the rapid test device; determine if a result of the rapid test device is valid; present an invalid-test-result notification to the user if the result of the rapid test device is invalid; determine a quantitative level of the result of the rapid test device if the result of the rapid test device is valid; and present the quantitative level of the result to the user.

Other embodiments of the disclosure are directed towards a rapid test results imaging method for determining the intensity of the test line. The method includes: capturing one or more first images of a lateral flow assay cassette using an image capture system with a display screen; presenting the one or more images to a user on the display screen with alignment bars as the one or more first images are being captured; employing a first artificial intelligence mechanism to determine a position of the lateral flow assay cassette in the one or more first images relative to the alignment bars; in responsive to determining that the position of the rapid test device relative to the alignment bars is not in an acceptable range, prompting the user of the image capture system to reposition the image capture system with respect to the alignment bars; determining, via a tilt detection system, a tilt angle of the image capture system with respect to horizontal; in responsive to determining that the tilt angle of the image capture system relative to horizontal is not in an acceptable range, prompting the user of the image capture system to rotate the image capture system relative to horizontal; in responsive to determining the tilt angle of the image capture system is appropriate, the automatic detections of blur levels in the image and triggering re-autofocus of the device as needed; responsive to the acceptable blur limits and position of the lateral flow assay cassette being in an acceptable range relative to the alignment bars in at least one of the one or more first images, and responsive to the tilt angle of the image capture system being in an acceptable range relative to horizontal: capturing one or more second images of the lateral flow assay cassette; employing a second artificial intelligence mechanism on the second image to determine if a result of the lateral flow assay cassette is valid; presenting an invalid-test-result notification to the user if the result of the lateral flow assay cassette being invalid; employing a third artificial intelligence mechanism on the second image to determine the qualitative status of the rapid test result (e.g., Positive or Negative); the determination of a quantitative amount of a analyte (e.g., antibody, antigen, etc.) in the lateral flow assay cassette if the result of the lateral flow assay cassette being valid; and presenting the qualitative test status and the quantitative amount of the analyte to the user.

In another aspect of some embodiments, the rapid test results imaging method further includes: determining the intensity of the control line by analytical methods comprising integrating grayscale images around the control line and determining the peak value present in the control line; determining the intensity of the test line by analytical methods comprising integrating grayscale images around the test line and determining the peak value present in the test line; determining the ratio of the test line peak value to the control line peak value; and using the determined ratio to present the presence of a quantitative amount of the analyte in the result to the user.

BRIEF DESCRIPTION OF THE SEVERAL VIEWS OF THE DRAWINGS

Non-limiting and non-exhaustive embodiments are described with reference to the following drawings. In the drawings, like reference numerals refer to like parts throughout the various figures unless otherwise specified.

For a better understanding of the present disclosure, reference will be made to the following Detailed Description, which is to be read in association with the accompanying drawings:

FIG. 3C illustrates a page of the rapid test results system with the user prompted to confirm acceptance with a Patient Profile Agreement.

FIGS. 4A and 4B illustrates a page of the rapid test results system with the user prompted to enter new patient information.

FIGS. 25A-25D illustrate use case examples of graphical user interfaces presenting information to a user with respect to validating rapid test device results in accordance with embodiments described herein.

DETAILED DESCRIPTION

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, or embodiments combining software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

Figure 1A:
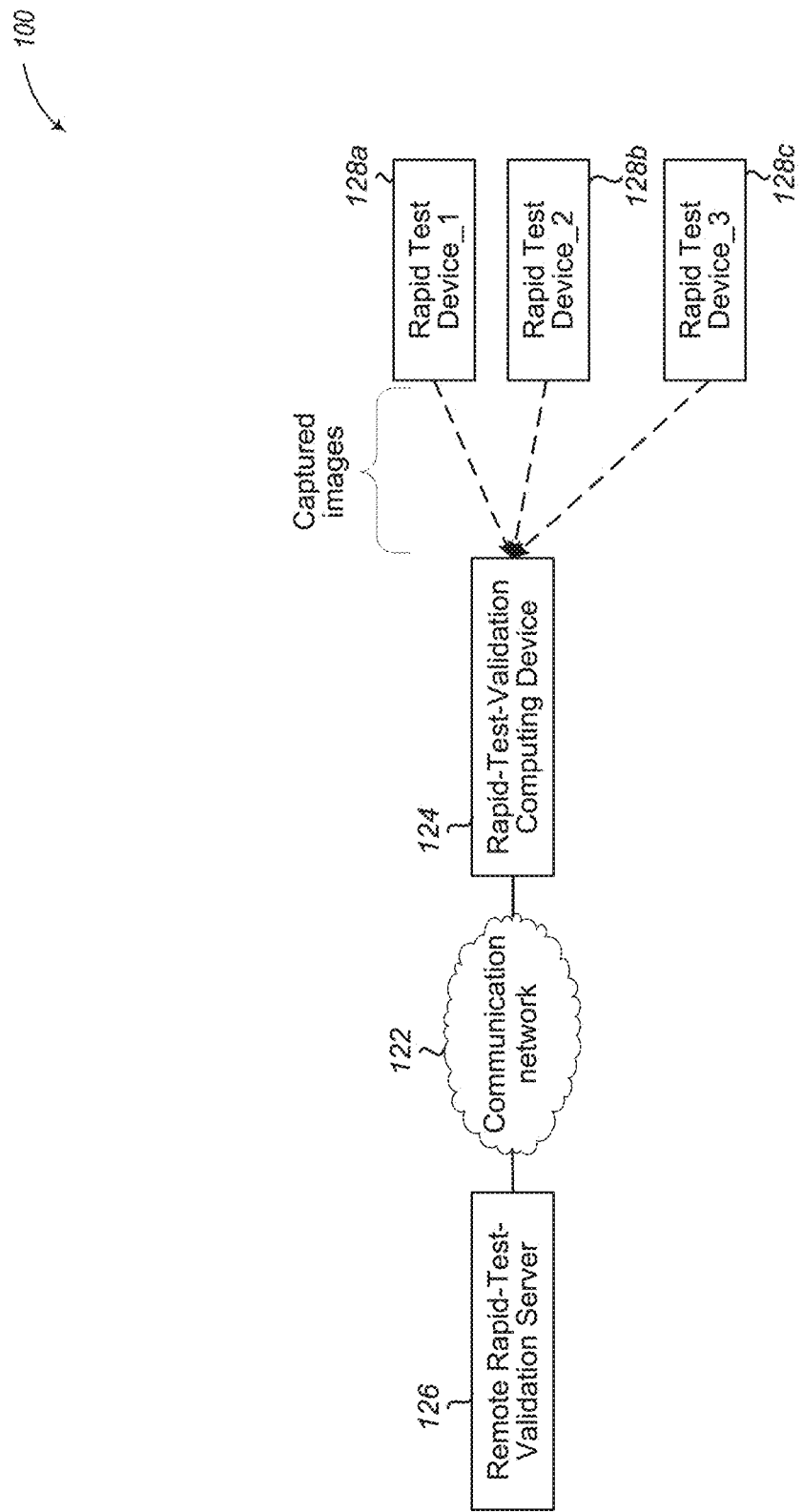
FIG. 1A illustrates a context diagram of an environment for validating rapid test device results in accordance with embodiments described herein.

FIG. 1A illustrates a context diagram of an environment 100 for validating rapid test device results (e.g., lateral flow assay results) in accordance with embodiments described herein. Environment 100 includes a rapid-test-validation computing device (e.g., lateral flow assay validation computing device, hereinafter "reader") 124 and one or more rapid test devices (e.g., lateral flow assay cassettes) 128a-128c (individually and collectively referred to as lateral flow assay cassette 128).

In some embodiments, the rapid test devices 128a-128c are testing devices that present visual cues as to a particular result. In general, the rapid test devices 128a-128c present an output in response to the presence or absence of a biologically relevant target. Examples of the rapid test devices 128a-128c may include, but are not limited to, a lateral flow immunoassay, flow-through assay, ELISA plate or other similar test device comprising a colorimetric, fluorometric, or other optically sensitive reagent that is indicative of the presence or absence of a biologically relevant target (e.g., a protein, nucleic acid sequence, antibody, virus, etc.).

In one or more embodiments, the rapid test devices 128a-128c include one or multiple test lines, one or multiple side-by-side dipsticks, or one or multiple side-by-side cassettes, or the like. In some embodiments, the rapid test devices 128a-128c may include arrays of spots, lines or other relevant shapes necessary for the test devices. Although embodiments described herein describe the rapid test devices 128a-128c as indicating whether a biologically relevant target is present or absent, embodiments are not so limited and the rapid test devices 128a-128c may also be used to indicate other reactive targets, such as pH levels (e.g., in soil), chlorine levels (e.g., in pools), and the like. In some embodiments, the rapid test devices are lateral flow assay cassettes 128a-128c, and the test performed is a lateral flow assay for neutralizing antibodies nAbs, as described herein.

Figure 1B:
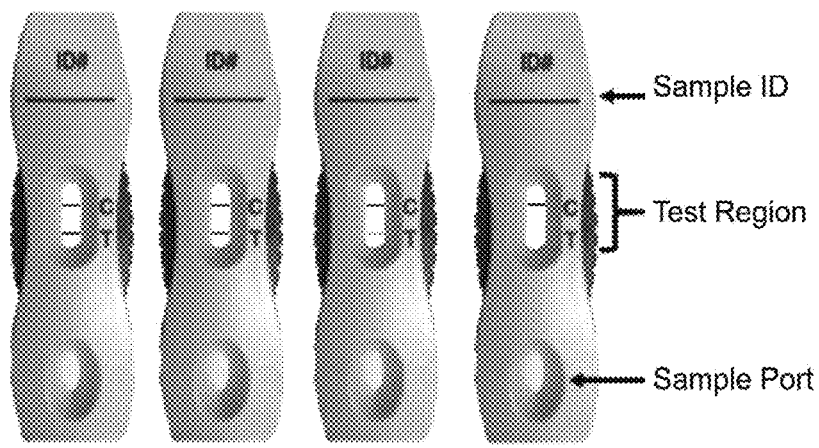
FIG. 1B depicts lateral flow assay cassettes used in a typical lateral flow assay where the cassettes illustrate negative, low positive, medium positive, and strong positive results.
Figure 28:
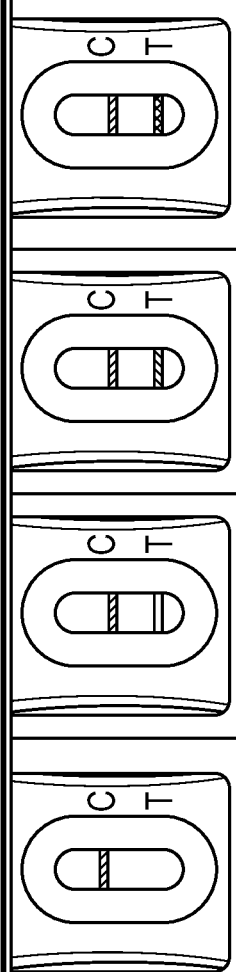
FIG. 28 depicts representative images captured by a smartphone app of SARS-CoV-2 lateral flow neutralizing antibody (NAb) assay cassettes according to the present disclosure along with PRNT titers, LFE values, and interpreted results.

Referring now to FIG. 1B, four potential typical lateral flow assay results are shown in which a visible control line demonstrates assay function, and the darkness of the test line varies. In some embodiments, a user may simply rely on the presence or absence of a visible test line to determine whether any neutralizing antibodies are present. For example, in one or more embodiments depicted in FIG. 1B, the user may compare the test line to a key that shows different darkness degrees of test lines that correlate with semi-quantitative results, such as the sample being low positive, medium positive, or strong positive. Notably, the test line signal strength for a neutralizing antibody (NAb) assay cassette (which is a competitive assay) is inverted (as shown in FIG. 28) when compared to typical lateral flow assay formats.

In other embodiments, the test lines may be read by a reader 124 that quantifies the darkness of the test line and, optionally, also the control line. The reader 124 may provide a quantitative or semi-quantitative result reflecting the amount of potency of nAbs in the sample. The reader 124 may use a calibration curve for a given assay type, a given assay lot, and/or a given reader 124. The calibration curve may also rely in part on the darkness of the control line.

In some embodiments, the test line and control line may be read by a reader 124 (e.g., smartphone application) to quantify the test and control line signal strength (e.g., peak or integrated values). The ratio of the test and control lines may then be calculated to provide a consistent metric which accounts for varying light sources, angles of operation, camera characteristics, and the like.

In some embodiments, the reader 124 may be a phone application or other program easily implemented by a point-of-care, home, or in-the-field user. In some embodiments, the ratios and thresholds for test positivity may be lot dependent and may be remotely determined and set (e.g., on a remote server) where the reader 124 may pull updated information regarding any specific test lot.

In some embodiments, an artificial intelligence-based reader 124 may be used. In the context of such a reader 124, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, or embodiments combining software and hardware aspects.

The reader 124 captures one or more images of the lateral flow assay cassette 128 via a camera (not illustrated). The reader 124 utilizes a first artificial intelligence mechanism to determine if a position of the lateral flow assay cassette 128 in the captured images is acceptable for processing, such as if it is in a particular position or within a threshold variance of a reference position. For example, the reader may use an auto-leveler function to ensure the lateral flow assay cassette is within a tolerable variance of being parallel to the camera. In some embodiments, the reader 124 may also augment the captured images by overlaying a semi-transparent reference or representation of the lateral flow assay cassette 128 to enable the user to properly align the reader 124 with the lateral flow assay cassette 128. In some embodiments, a plurality of images are captured and displayed to the user in real time to allow the user to move the position of the lateral flow assay cassette 128 or the reader 124 for proper alignment.

Although embodiments are described herein as using an artificial intelligence mechanism to determine a position of the rapid test device (or a color validation sheet), embodiments are not so limited. Rather, other techniques for tracking objects in images may be used, such as edge or shadow detection.

In some embodiments, the reader 124 may utilize the previously captured image that included the properly aligned lateral flow assay cassette 128 for further processing. In other embodiments, the reader 124 may capture another image in response to manual user input or automatically, such as when the lateral flow assay cassette 128 is properly aligned.

If the lateral flow assay cassette 128 is positioned properly in at least one of the captured images, the reader 124 utilizes a second artificial intelligence mechanism on the image to determine if a result of the lateral flow assay cassette 128 is valid or invalid. For example, if the control line is not present or is too faint, the result may be determined to be invalid and the user instructed to repeat the assay with a different lateral flow assay cassette and possibly also a different sample.

If the result is valid, the reader 124 may utilize a third artificial intelligence mechanism on the image to determine a quantitative level of the results (e.g., "positive," "negative," a semi-quantitative indicator, or a quantified amount, and the like). The objective characterization may be determined as described above using the darkness of the test line and, in some instances, also the control line. In one embodiment, the third may use the second image to determine the intensity of the control line by analytical methods that may include integrating grayscale images around the control line and determining the peak value present in the control line, determine the intensity of the test line by analytical methods including integrating grayscale images around the test line and determining the peak value present in the test line, determine the ratio of the test line peak value or the integrated test line value to the control line peak value or integrated control line value, and then use the determined ratio to present the presence or absence of and/or a semi-quantitative or quantitative amount of neutralizing antibody in the sample result to the user.

The reader 124 displays the objective characterization of the results to a user of the reader 124. The reader 124 also displays information indicating if the result of the lateral flow assay cassette 128 is valid or invalid.

In some embodiments, the reader 124 may omit the use of the second artificial intelligence mechanism and may not present information indicating if the result of the lateral flow assay cassette 128 is valid or invalid. In such embodiments, the user may be instructed to determine if a control line is visible and to disregard assay results if it is not. Alternatively, in such embodiments, the third artificial intelligence may be unable to present results, particularly if, as described above, the determining the results requires the presence of a control line to calculate a ratio.

In some embodiments, the reader 124 determines and displays the quantitative level of the results and the valid/invalid determination in real time as the user is using the reader 124 to capture images of the lateral flow assay cassette 128. In other embodiments, the reader 124 may capture images of one or more lateral flow assay cassettes 128 for post-processing and display to a user. In various embodiments, the reader 124 may transmit or upload the validation and objective results, along with the captured images, to one or more other computing devices for storage or review. The results may be associated with a sample identifier, for example, a sample ID input by the user or scanned by the reader from the lateral flow assay cassette.

Results can be used to further train or refine the artificial intelligence mechanisms used herein. Examples of such other computing devices may include remote server 126, cloud computing resources, or other remote computing devices that maintain patient data. In some embodiments, an identifier or lot number of the lateral flow assay cassette may be stored with the results, which can be used to determine if a particular lateral flow assay cassette lot or batch is defective, e.g., due to erroneous results.

In some embodiments, a user may use the reader 124 to select a lateral flow assay cassette for processing. The user may select the appropriate lateral flow assay cassette from a list of possible lateral flow assay cassettes or the user may scan a machine readable symbol (e.g., barcode, QR code, and the like) or other identifier of the lateral flow assay cassette. In at least one embodiment, the reader 124 may be configured to start or utilize a timer for the selected lateral flow assay cassette. For example, if the lateral flow assay cassette requires 20 minutes to complete the assay and output a result, then the reader 124 may utilize a timer so as to not process the lateral flow assay cassette until after the timer has expired. In this way, the reader 124 does not process a lateral flow assay cassette and output a result before the lateral flow assay cassette has completed its assay. Likewise, the same timer or a second timer may establish a window of time in which to process the lateral flow assay cassette. This time window may be used to ensure the lateral flow assay cassette is not process too late.

Examples of the reader 124 include, but are not limited to, smartphones, tablet computers, desktop or laptop computers in communication with a camera, wearable computers, or other computing devices that have or are in communication with a camera.

In some embodiments, the environment 100 may optionally include a server 126. However, in many embodiments, all of the operations are performed in the reader 124 without requiring the use of or communication with the server 126. In various embodiments, the remote server 126 may perform many of the embodiments described herein as being performed by the reader 124. In at least one embodiment, the reader 124 may capture images of the lateral flow assay cassettes 128 and transmit the captured images to the remote server 126 via communication network 122 for processing. The communication network 122 includes one or more wired or wireless, or a combination of wired and wireless, data communication networks. The remote server 126 may output the results to a user via a display device (not illustrated) or may transmit the results back to the reader 124 for display. In some embodiments, the remote server 126 is able to query whether or not an updated machine learning classification system is available and may update the machine learning classification system if one is available.

Figure 2:
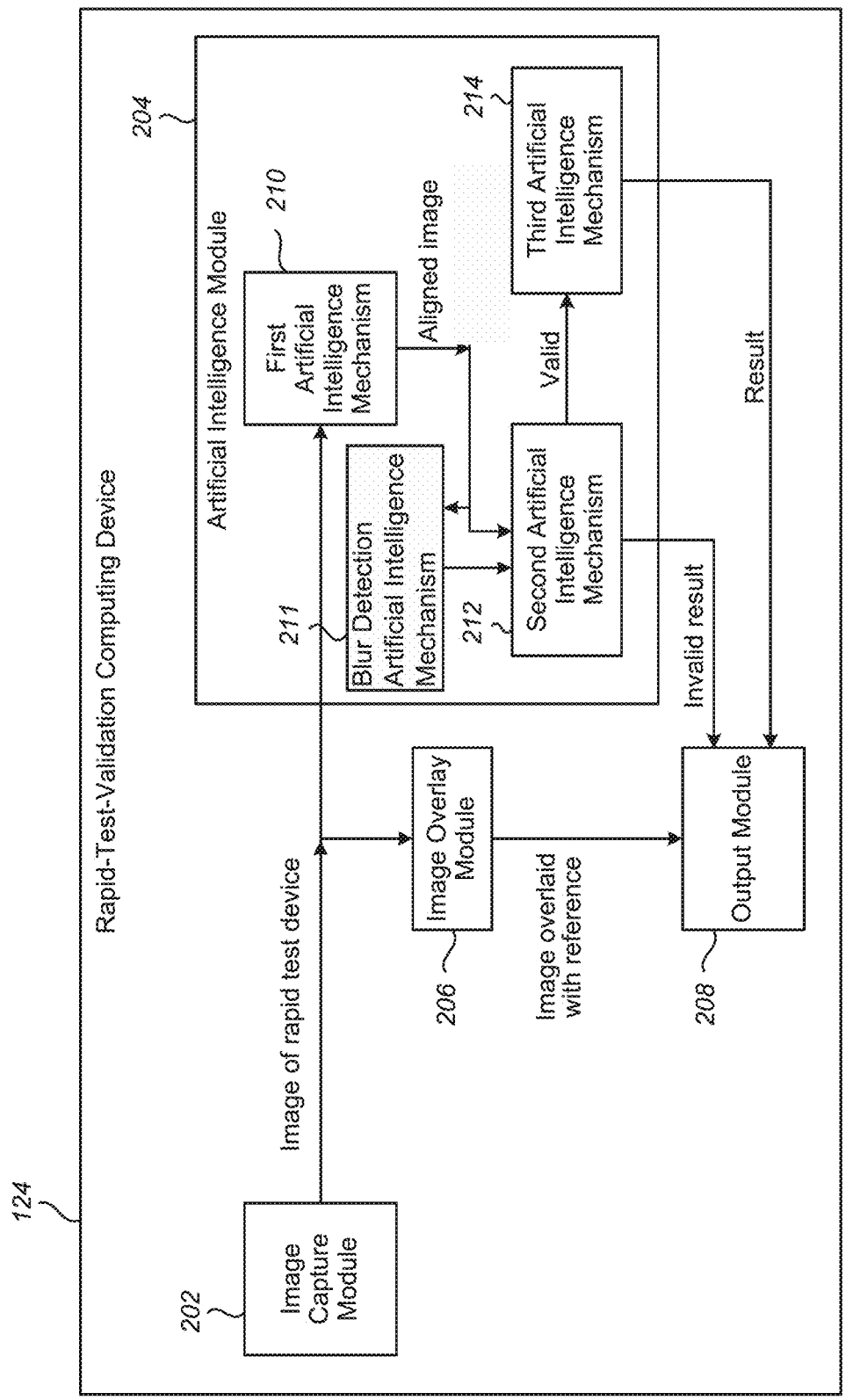
FIG. 2 illustrates a system diagram of a rapid-test-validation computing device in accordance with embodiments described herein.

FIG. 2 illustrates a system diagram of a reader 124 (e.g., rapid-test-validation computing device) in accordance with embodiments described herein. The system components of the reader 124 illustrated in FIG. 2 are for illustrative purposes and are not to be limiting. Moreover, the functionality of one or more of the illustrated system components may be combined into fewer components or separated in more components than what is shown.

In one or more embodiments, the reader 124 includes an image capture module 202, an artificial intelligence module 204, an image overlay module 206, and an output module 208. The image capture module 202 performs embodiments described herein to capture or obtain images of one or more rapid test devices. The captured images are provided from the image capture module 202 to the artificial intelligence module 204 and to the image overlay module 206. In some embodiments, the image overlay module 206 modifies or augments the captured images to overlay a semi-transparent reference or representation of the rapid test device. The modified images are provided from the image overlay module 206 to the output module 208 for presentation to a user.

In some embodiments, the artificial intelligence module 204 includes a first artificial intelligence mechanism 210, an optional blur detection artificial intelligence mechanism 211, a second artificial intelligence mechanism 212, and a third artificial intelligence mechanism 214. The first artificial intelligence mechanism 210 determines if the rapid test device is properly aligned in the captured image. The optional blur detection artificial intelligence mechanism 211 determines if there is an unacceptable amount of blurriness in the captured image of the rapid test device, using the machine learning classification system which is training on distinguishing blurry images from non-blurring images. If it is determined by the optional blur detection artificial intelligence mechanism 211 that there is an un-acceptable amount of blurriness in the captured image, then the system prompts the user to take a replacement image.

The second artificial intelligence mechanism 212 determines if one or more results on the rapid test device are valid or invalid. If the results are invalid, the artificial intelligence module 204 presents the invalid determination to a user via the output module 208. The third artificial intelligence mechanism 214 determines a quantitative level of the valid results. The artificial intelligence module 204 presents the quantitative level of the results to the user via the output module 208. In some embodiments, the artificial intelligence module 204 may instruct the image capture module 202 to capture additional images of the rapid test device, such as if the rapid test device is not properly positioned in the captured images.

In some embodiments, the output module 208 displays information to a user of the reader 124 via a display device. In other embodiments, the output module 208 transmits the results information to another computing device, such as remote server 126, for display, storage, or further processing (e.g., comparing a plurality of results from a plurality of rapid test devices).

Figure 3B:
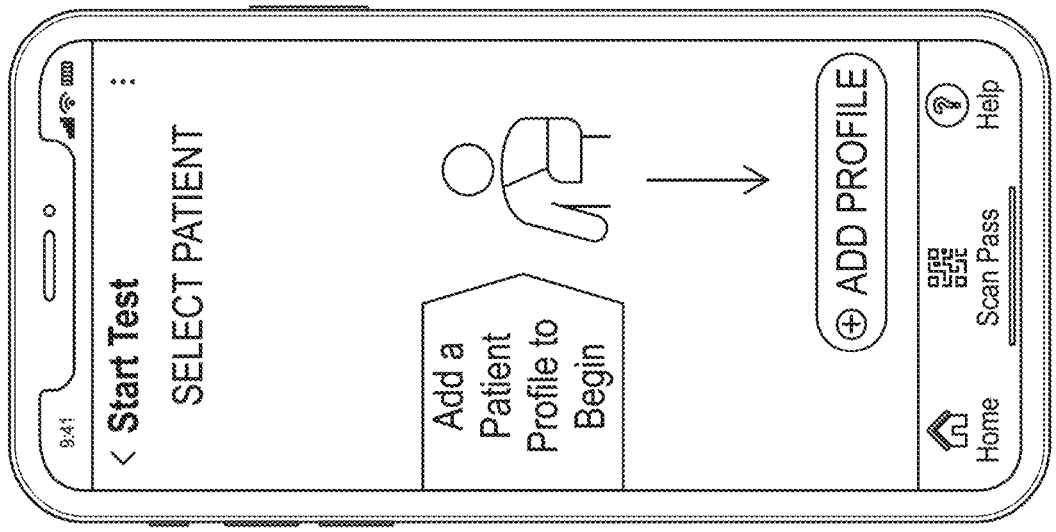
FIG. 3B illustrates a page of the rapid test results system with the "Start a New Test" selected, and the user prompted to add a patient profile.
Figure 3A:
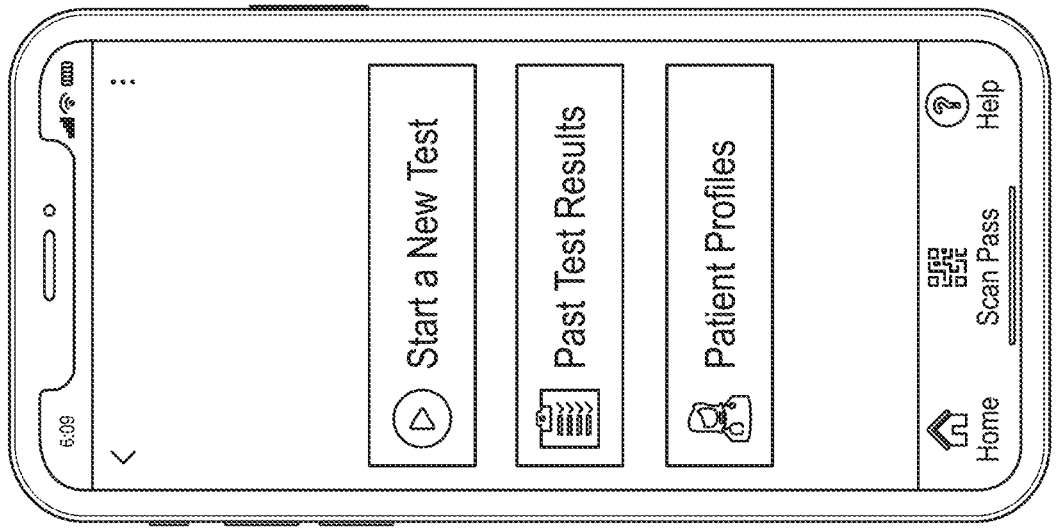
FIG. 3A illustrates a page of the rapid test results system with selection regions of "Start a New Test," "Past Test Results," and "Patient Profiles."
Figure 4B:
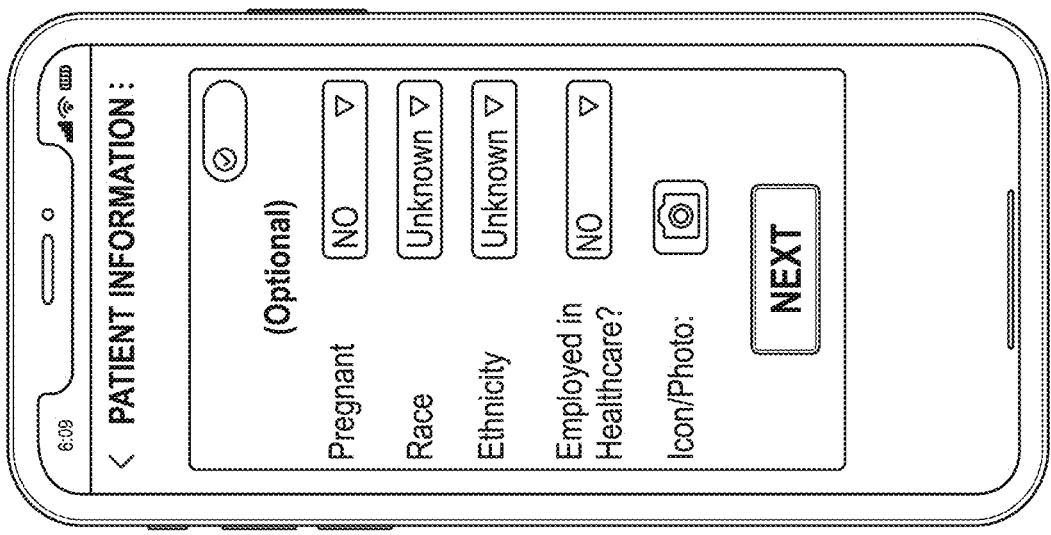

Referring now to FIGS. 3A-22B, in some embodiments, the reader 124 that is used to read the test line and control line includes a rapid test device application with enhanced image capture on a smartphone (i.e., rapid test results system). As shown in FIG. 3A, in some embodiments, the rapid test results system has a page with selection regions to "Start a New Test," "Past Test Results," and "Patient Profiles." If a user selects the "Start a New Test" region, then the page shown in FIG. 3B is displayed in which a user is prompted to add a patient profile. Referring now to FIG. 3C, the user is prompted to confirm acceptance with a Patient Profile Agreement. After confirming acceptance of the Patient Profile Agreement, the user is prompted to enter new patient information, as shown in FIGS. 4A and 4B.

Figure 5:
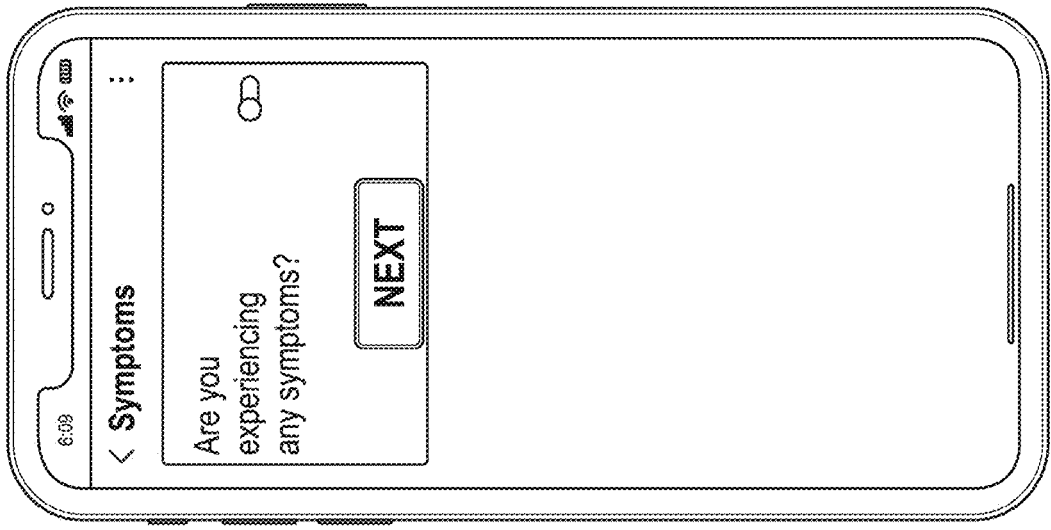
FIG. 5 illustrates a page of the rapid test results system with the user prompted to confirm whether or not they are experiencing any symptoms of an illness for which they are being tested.

As shown in FIG. 5, in some embodiments, the user is prompted to confirm whether or not they are experiencing any symptoms of an illness for which they are being tested, e.g., COVID-19. Continuing, FIG. 6 displays a list of symptoms for the user to confirm whether or not they are currently experiencing the symptoms. In some embodiments, this list includes, by way of example only and not by way of limitation, fever, feeling feverish, chills, cough, shortness of breath, difficulty breathing, fatigue, muscle or body aches, headache, loss of taste, loss of smell, and sore throat.

Figure 7:
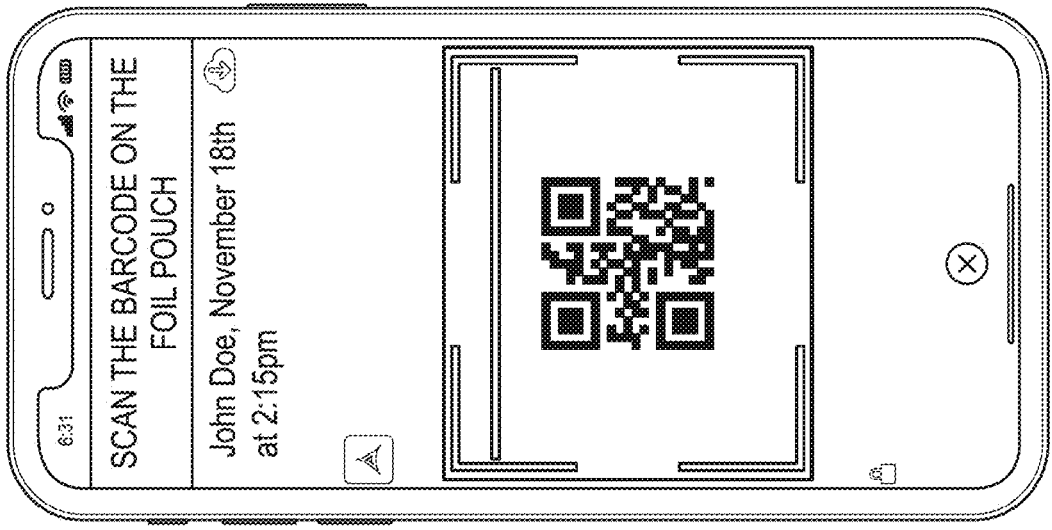
FIG. 7 illustrates a page of the rapid test results system that prompts the user to scan the bar code on the foil pouch using the scanner on the camera of the user's smartphone.
Figure 6:
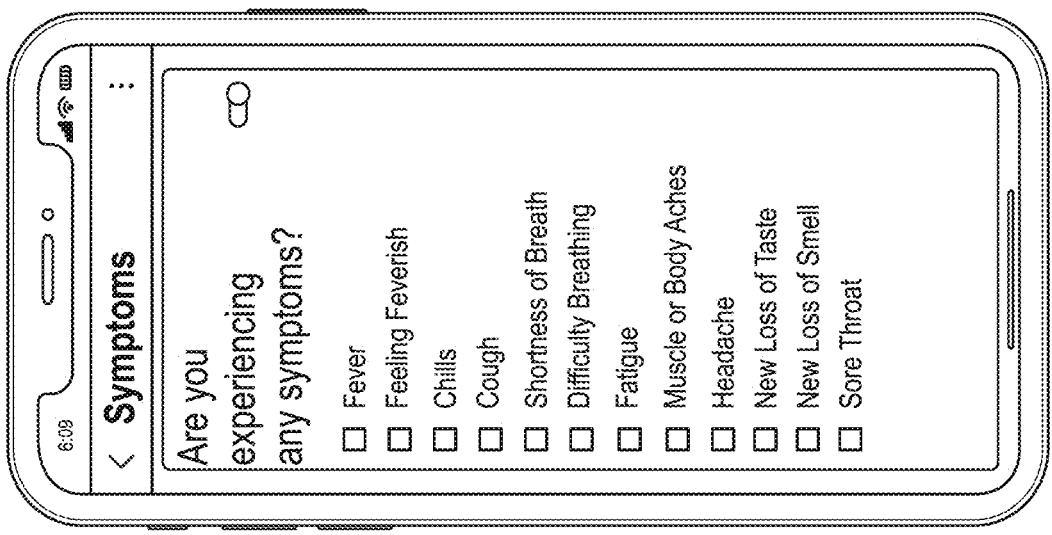
FIG. 6 illustrates a page of the rapid test results system that displays a list of symptoms for the user to confirm whether or not they are currently experiencing.
Figure 9:
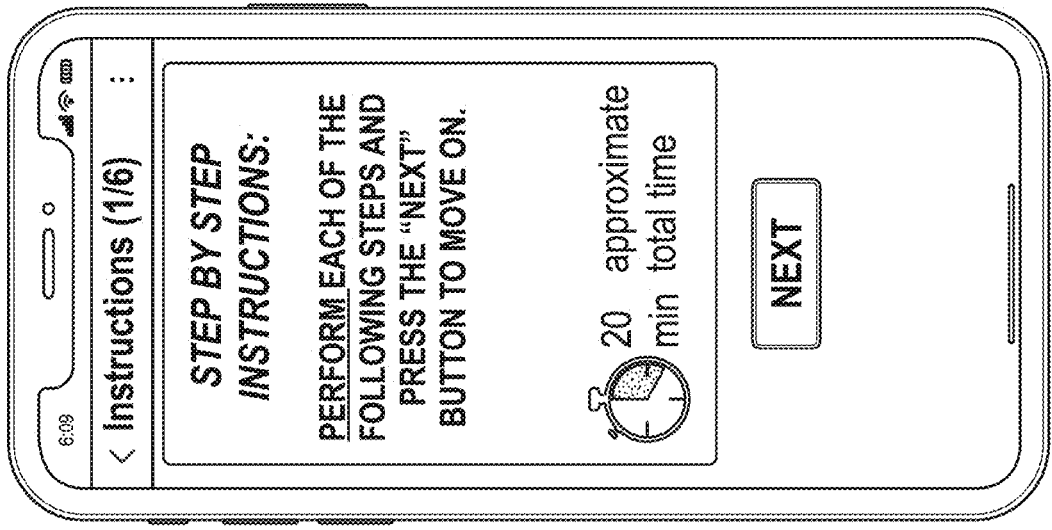
FIG. 9 illustrates a page of the rapid test results system that presents step-by-step instructions for performing the test.
Figure 8:
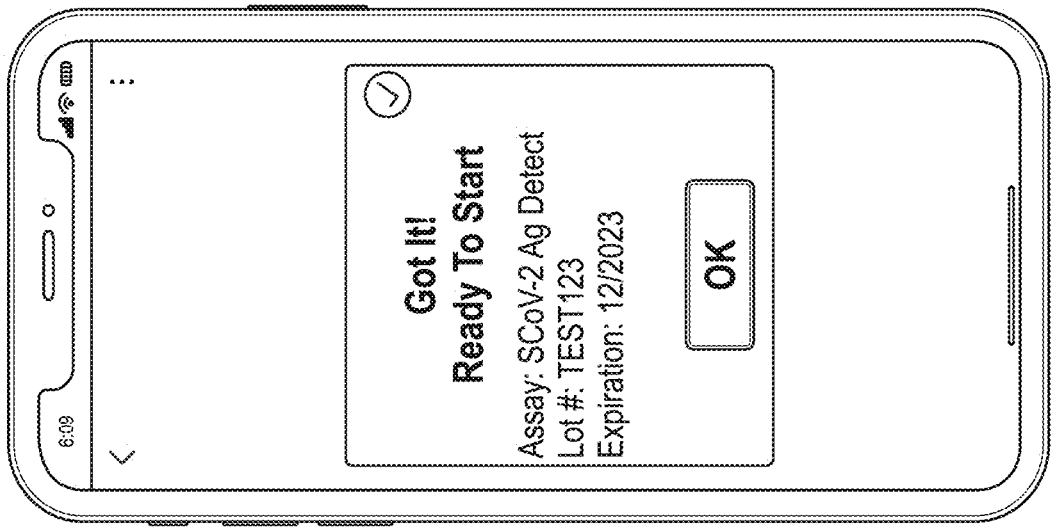
FIG. 8 illustrates a page of the rapid test results system that identifies the bar code and determines the assay, lot number, and expiration date from the bar code.

Referring now to FIG. 7, in some embodiments the user is prompted to scan the bar code on the foil pouch using the scanner on the camera of the user's smartphone. As shown in FIG. 8, in some embodiments the rapid test results system identifies the bar code (or other code, e.g., QR code, etc.) and determines the assay, lot number, and expiration date from the bar code. Next, as displayed in FIG. 9, in some embodiments the rapid test results system presents step-by-step instructions for performing the test. Specifically, in this embodiment the page shown in FIG. 9 instructs the user to perform each of the following steps and then press the "Next" button to move on to the next screen. This page also notes that the total test time in approximately 20 minutes.

Figure 11:
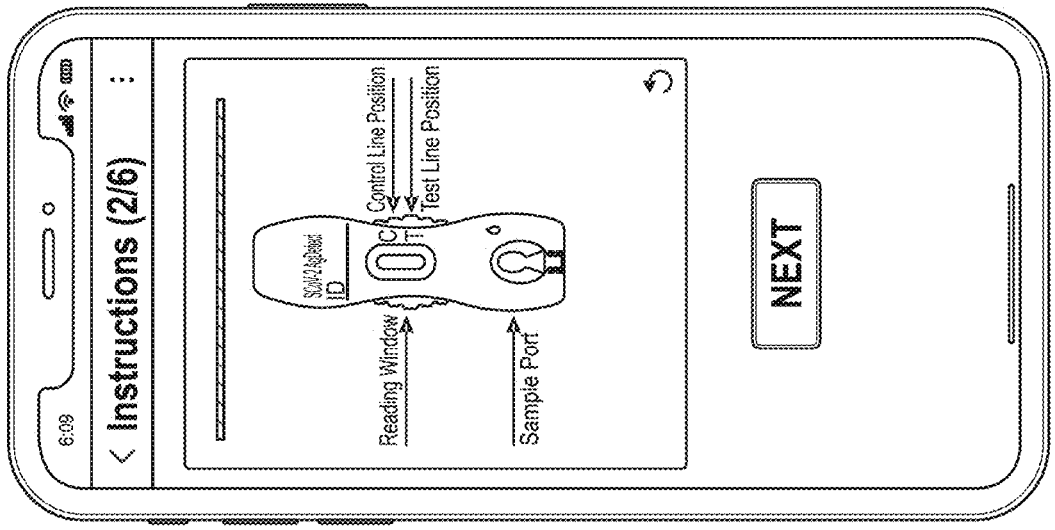
FIG. 11 illustrates a page of the rapid test results system that shows the testing device positioned on a flat surface with the reading window, the control line position, the test line position, and the sample port displayed.
Figure 10:
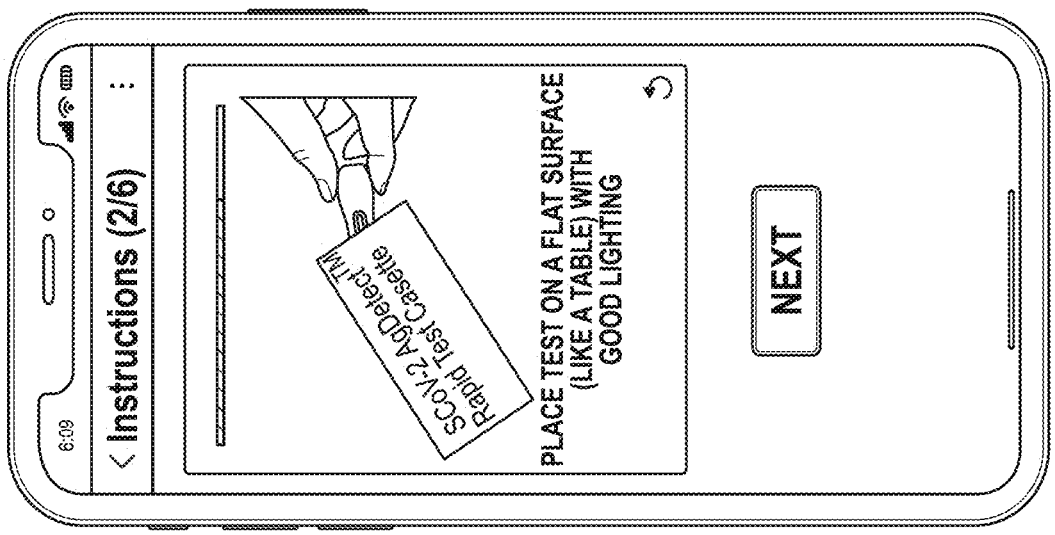
FIG. 10 illustrates a page of the rapid test results system that instructs the user to place the test on a flat surface with good lighting.
Figure 13A:
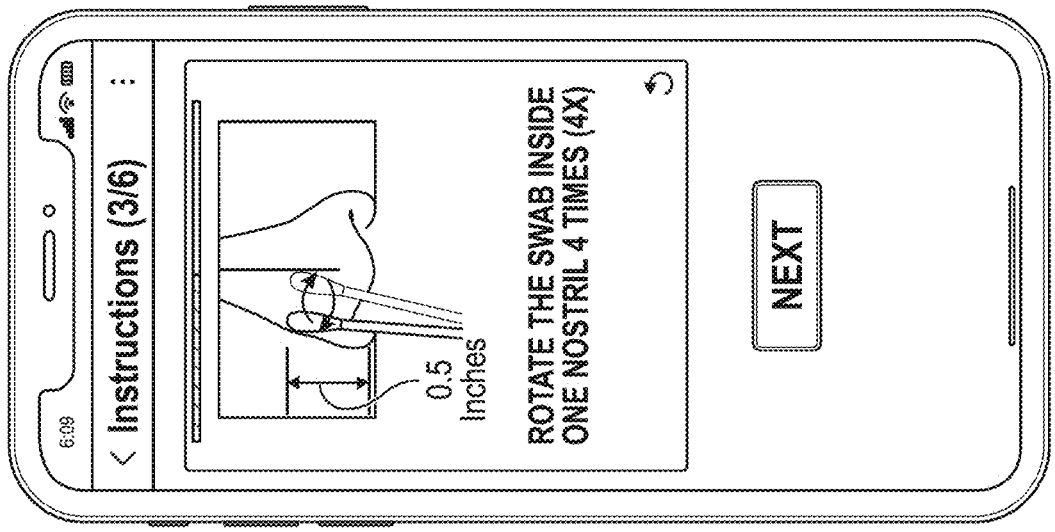
FIG. 13A illustrates a page of the rapid test results system that instructs the user to rotate the swab inside one nostril 4 times on the right side.
Figure 12:
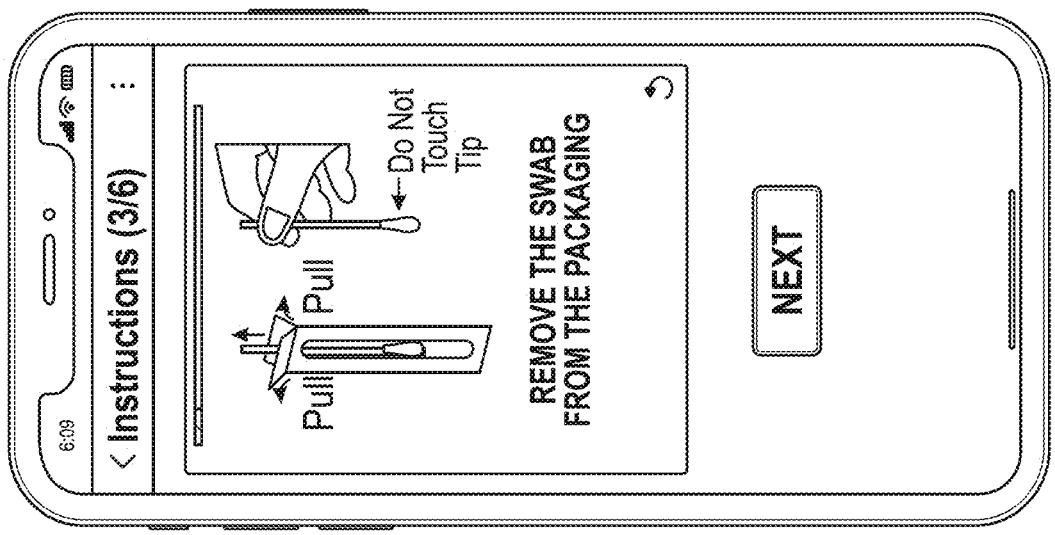
FIG. 12 illustrates a page of the rapid test results system that shows a swab being removed from the packaging with a warning for the user not to touch the tip of the swab.
Figure 13B:
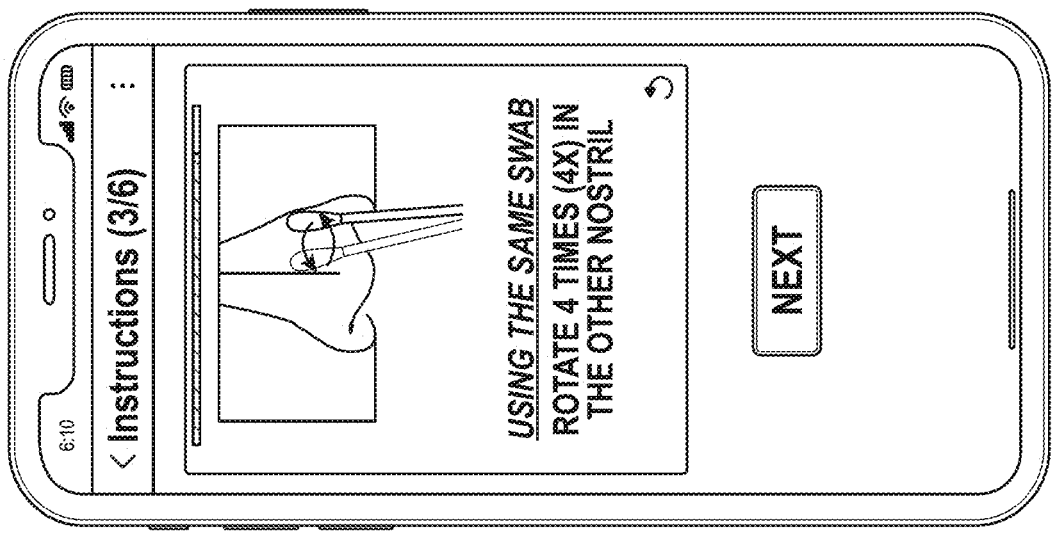
FIG. 13B illustrates a page of the rapid test results system that instructs the user to rotate the swab inside one nostril 4 times on the left side.
Figure 15A:
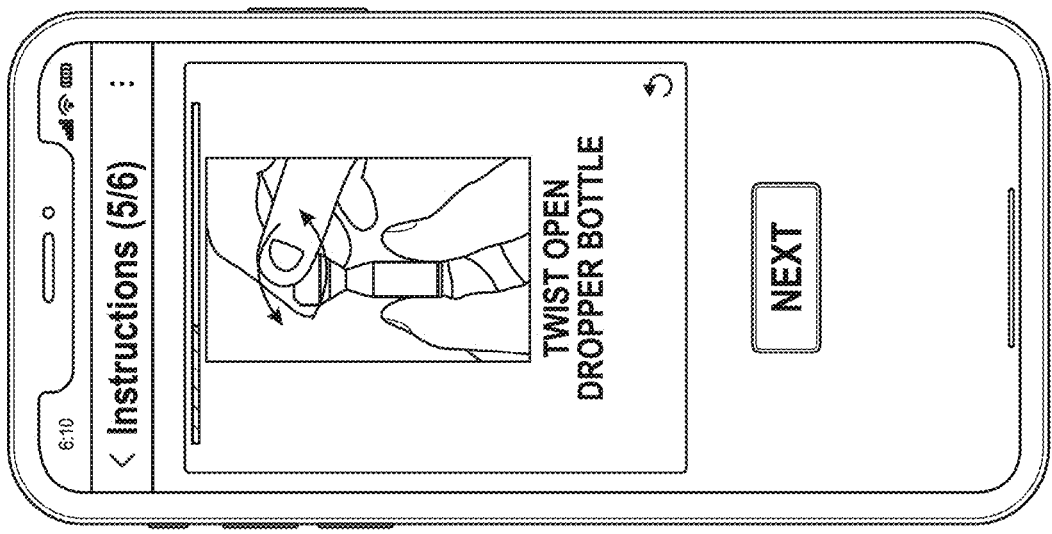
FIG. 15A illustrates a page of the rapid test results system that instructs the user to twist open the dropper bottle.

Referring now to FIG. 10, this page of the rapid test results system instructs the user to place the test on a flat surface with good lighting, and then select the "next" virtual button. Some embodiments of FIG. 11 show the test positioned on a flat surface with the reading window, the control line position, the test line position, and the sample port. Next, in some embodiments, FIG. 12 shows a swab being removed from the packaging with a warning for the user not to touch the tip of the swab. As shown in FIGS. 13A and 13B, in some embodiments the rapid test results system instructs the user to rotate the swab inside one nostril 4 times on the right side (in FIG. 13A) and to rotate the swab inside one nostril 4 times on the left side (in FIG. 13B).

Figure 14A:
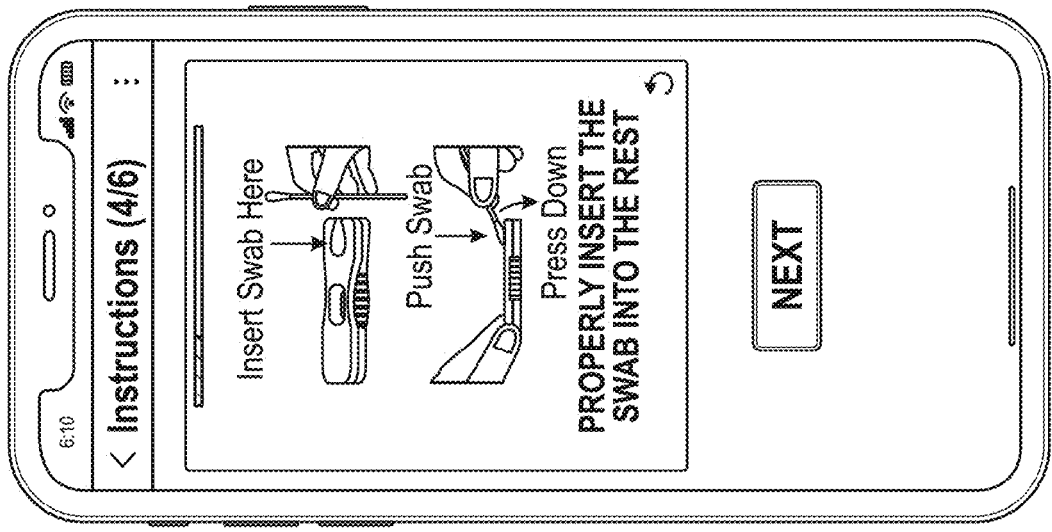
FIG. 14A illustrates a page of the rapid test results system that instructs the user to insert the swab into the end of the testing device and press down to properly insert the swab.
Figure 14B:
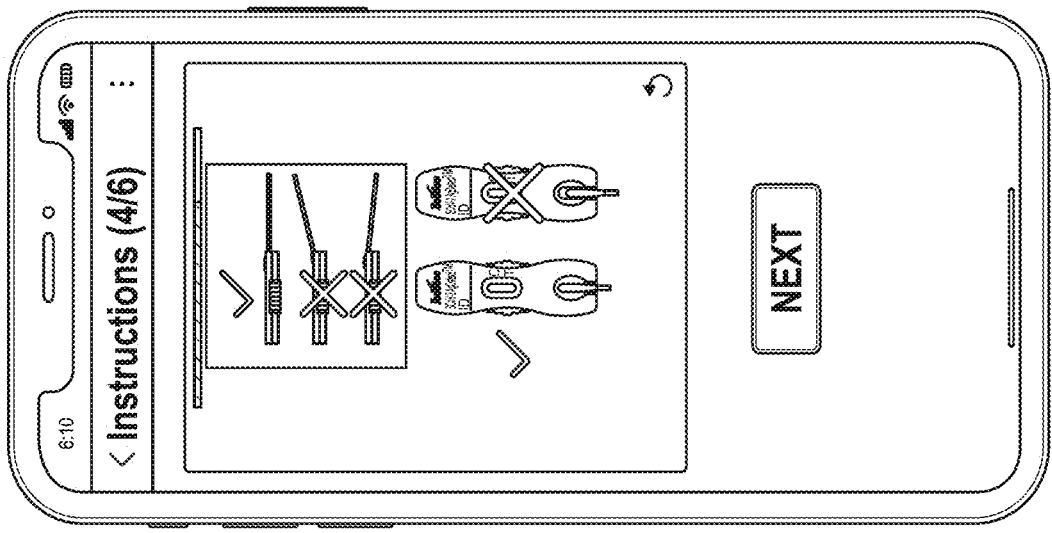
FIG. 14B illustrates a page of the rapid test results system that presents examples of the swab being properly inserted into the testing device, and also shows examples of the swab being improperly inserted into the testing device.
Figure 16:
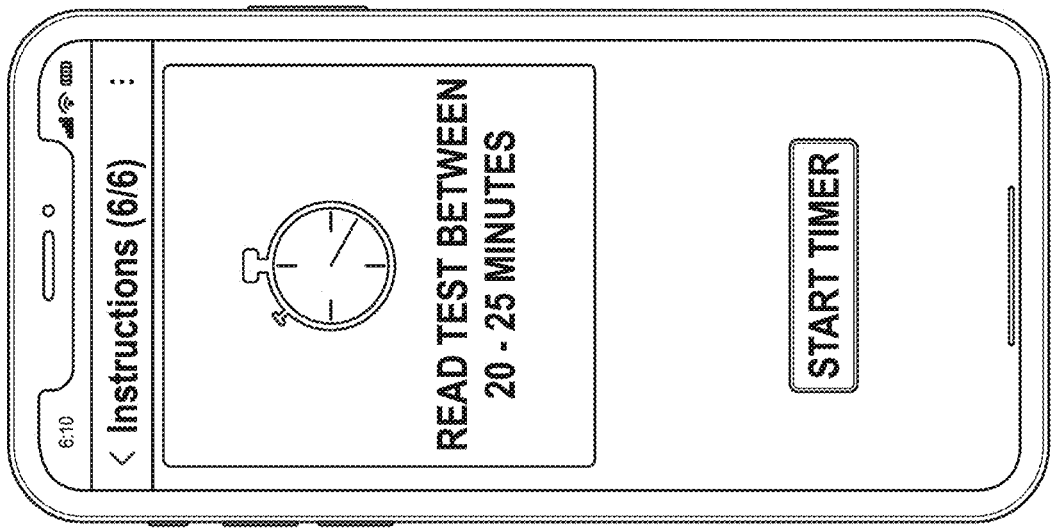
FIG. 16 illustrates a page of the rapid test results system that prompts the user to read the test results after 20-25 minutes.
Figure 15B:
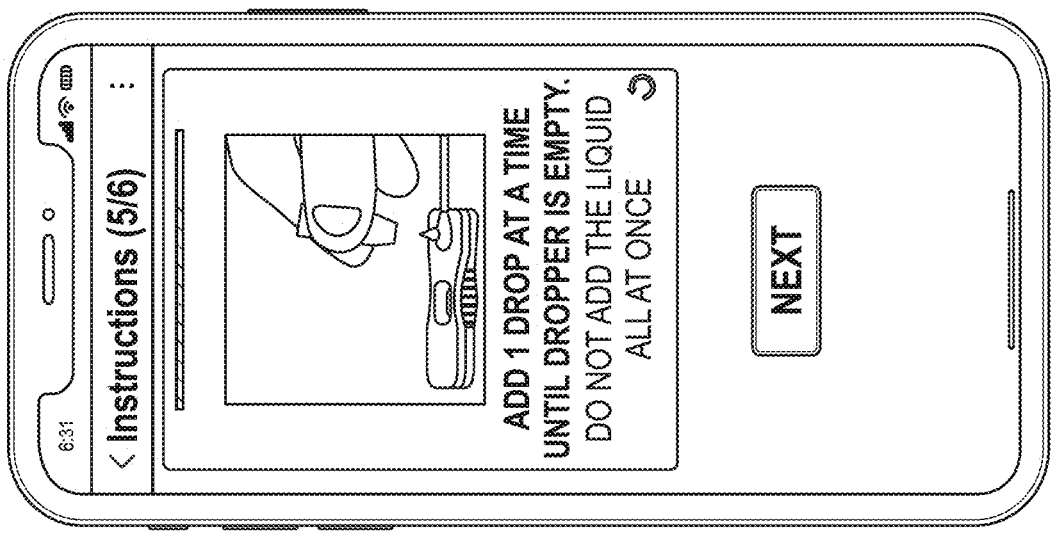
FIG. 15B illustrates a page of the rapid test results system that instructs the user to add one drop at a time until the dropper bottle is empty.

As shown in FIG. 14A, in one or more embodiments of the rapid test results system, the user is instructed to insert the swab into the end of the testing device and press down to properly insert the swab. Continuing, FIG. 14B shows examples of the swab being properly inserted into the testing device, and also shows examples of the swab being improperly inserted into the testing device. Next in FIG. 15A, in one or more embodiments of the rapid test results system, the user is instructed to twist open the dropper bottle. Continuing in FIG. 15B, in one or more embodiments of the rapid test results system, the user is instructed to add one drop at a time until the dropper bottle is empty. Finally in FIG. 16, the user is prompted to read the test results after 20-25 minutes.

Figure 17B:
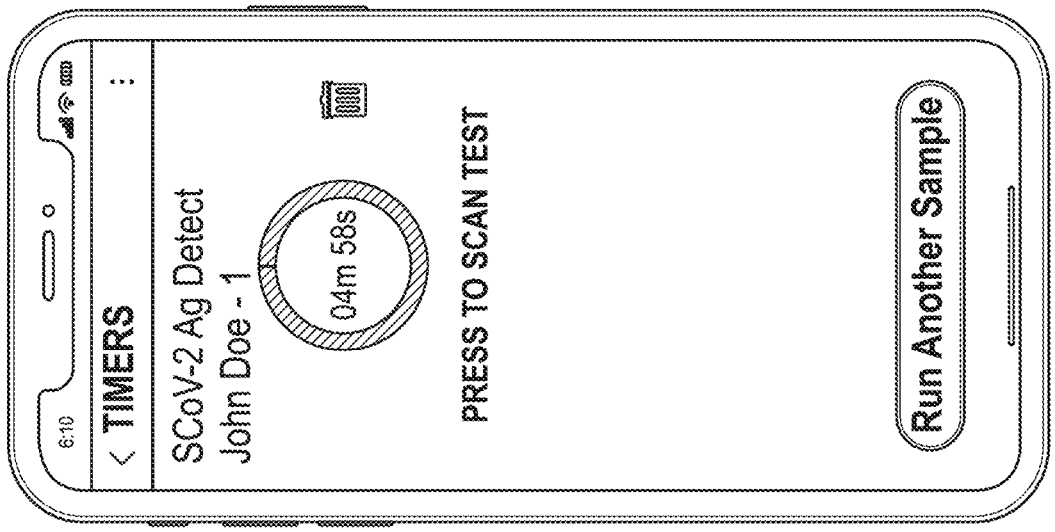
FIG. 17B illustrates a page of the rapid test results system that instructs the user to scan the test results since the user has waited an appropriate amount of time.
Figure 17A:
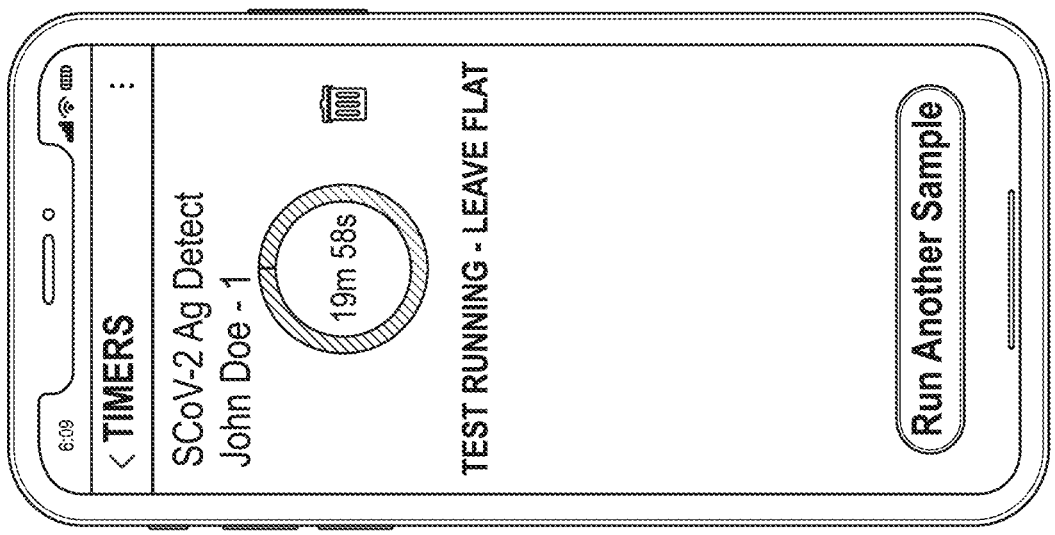
FIG. 17A illustrates a page of the rapid test results system that instructs the user that the test is running and to leave the testing device flat.

Referring now to FIG. 17A, this page of the rapid test results system instructs the user that the test is running and to leave the testing device flat. Continuing, in some embodiments as shown in FIG. 17B, this page of the rapid test results system instructs the user to scan the test results since the user has waited an appropriate amount of time (i.e., 20-25 minutes).

Figure 18B:
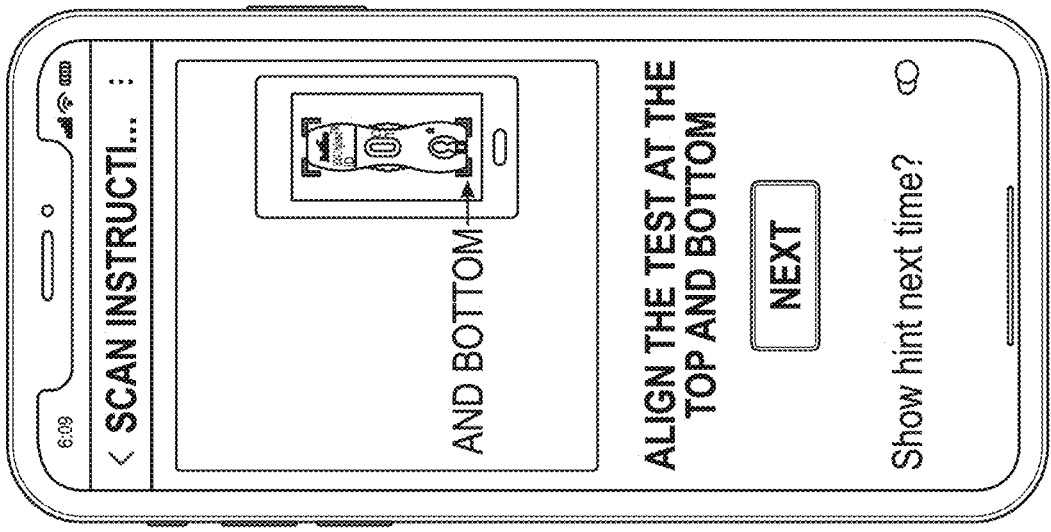
FIG. 18B illustrates a page of the rapid test results system that instructs the user to hold the camera of the smartphone over the testing device and align the test at the bottom of the alignment bars.
Figure 18A:
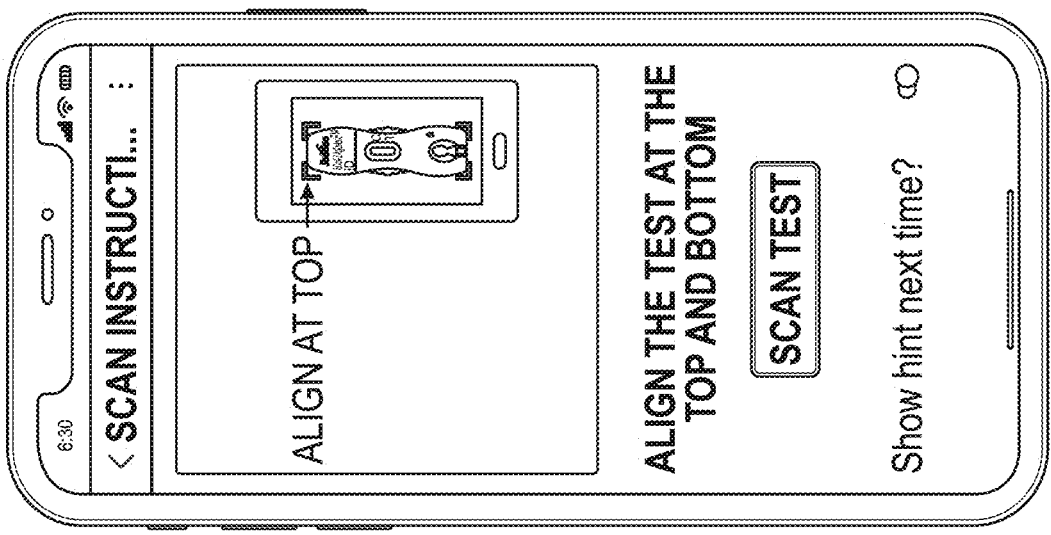
FIG. 18A illustrates a page of the rapid test results system that instructs the user to hold the camera of the smartphone over the testing device and align the test at the top of the alignment bars.
Figure 19A:
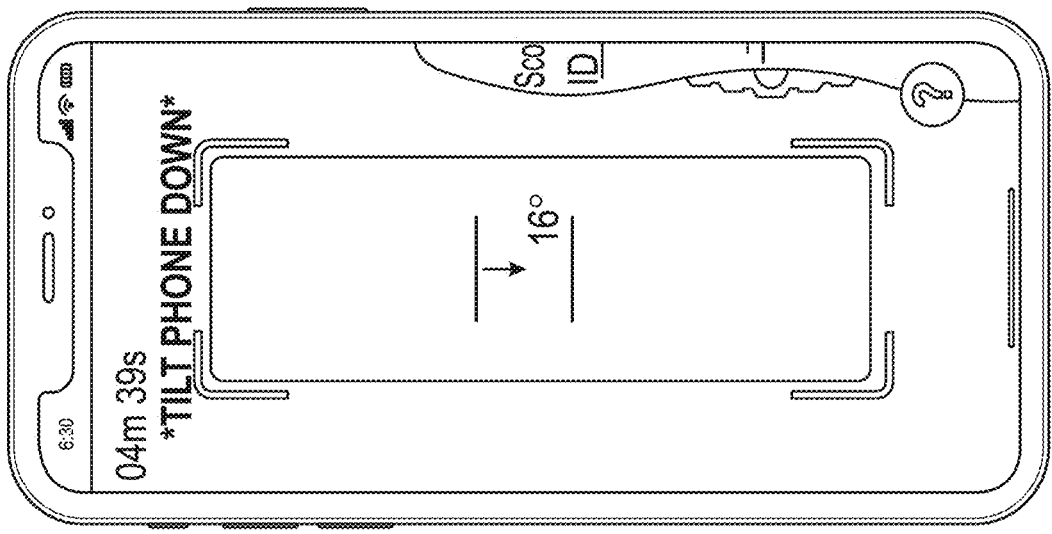
FIG. 19A illustrates a page of the rapid test results system that instructs the user to tilt the smartphone down a specific number of degrees to correctly align the testing device with the alignment bars.
Figure 18C:
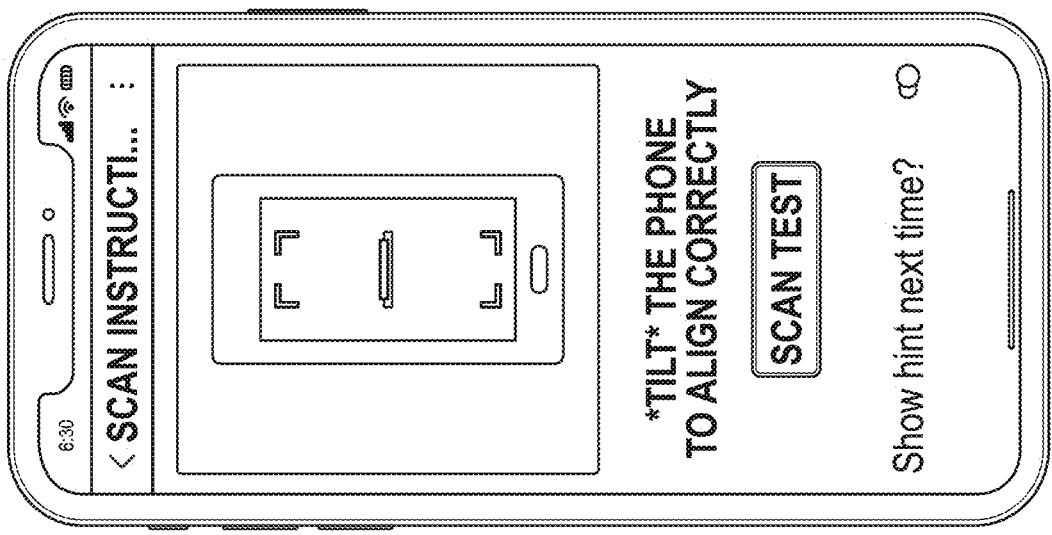
FIG. 18C illustrates a page of the rapid test results system that instructs the user to tilt the smartphone to correctly align the testing device with the alignment bars before selecting the "scan test" virtual button.

Referring now to FIGS. 18A and 18B, this page of the rapid test results system instructs the user to hold the camera of the smartphone over the testing device and align the test at the top and bottom of the alignment bars. Specifically, in FIG. 18A the rapid test results system instructs the user to align the test at the top of the alignment bars, while in FIG. 18B the rapid test results system instructs the user to align the test at the bottom of the alignment bars. Continuing, in FIG. 18C the rapid test results system instructs the user to tilt the smartphone in order to better align the testing device with the alignment bars before selecting the "scan test" virtual button. Next, the rapid test results system employs an accelerometer to determine the number of degrees that the user needs to tilt the smartphone and camera. As shown in FIG. 19A, the rapid test results system instructs the user to tilt the smartphone down 16 degrees to better align the testing device with the alignment bars. FIG. 19B shows the testing device aligned with the alignment bars after the user has tilted the smartphone down 16 degrees to improvement alignment.

Figure 19C:
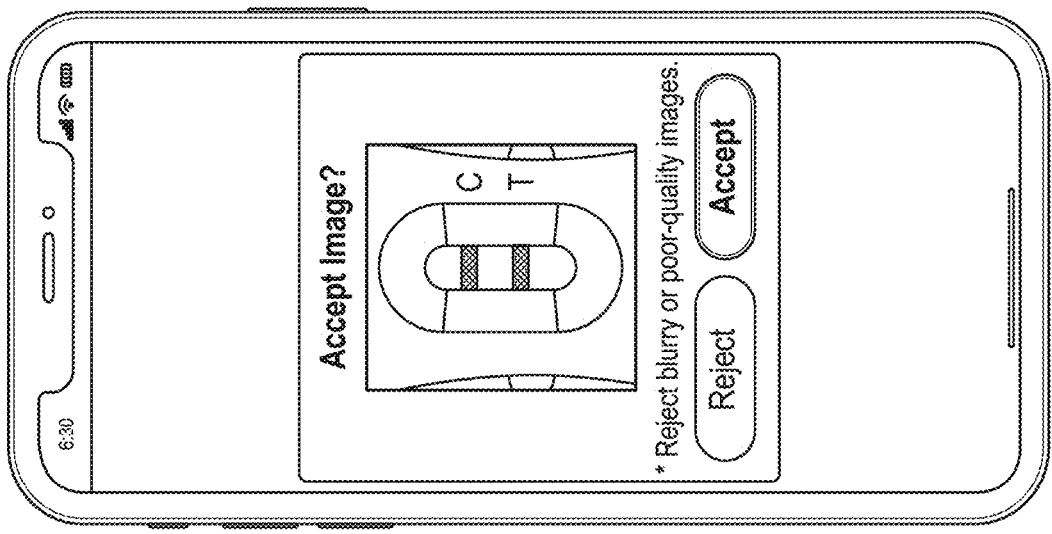
FIG. 19C illustrates a page of the rapid test results system that instructs the user to either accept or reject the scanned image of the test results.
Figure 19B:
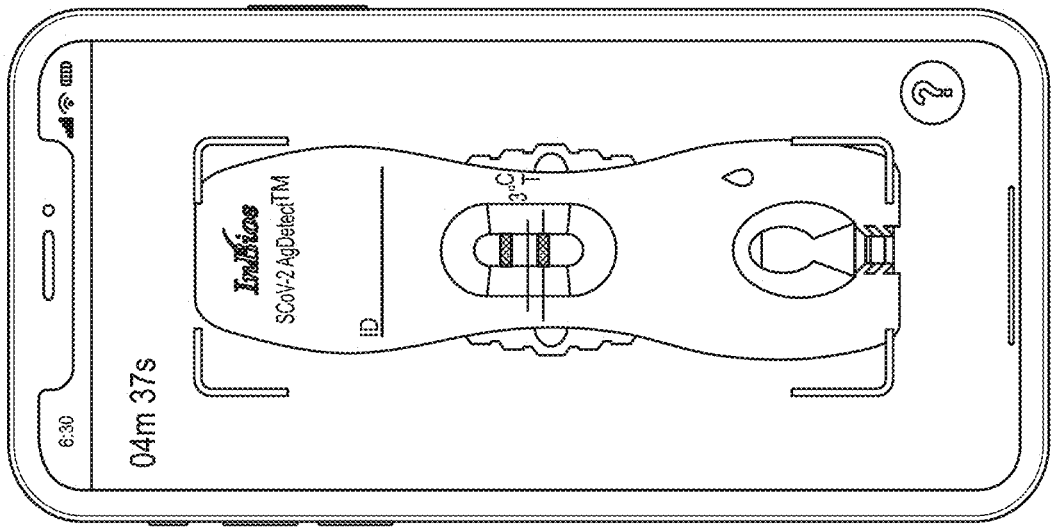
FIG. 19B illustrates a page of the rapid test results system that shows the testing device aligned with the alignment bars after the user has tilted the smartphone to improvement alignment.

FIG. 19C shows the rapid test results system instructing the user to either accept or reject the scanned image of the test results. For example, the scanned image of the test results would be rejected if the images were blurry or poor-quality, and would be accepted if the images were clear. Significant factors in the clarity of the images are lighting where the images are being scanned and the proper tilt angle of the smartphone camera being achieved by the user. In one or more embodiments, the rapid test results system interprets the results of the accepted images, including various levels of the test line results, so that the result does not simply provide a positive or negative result, but actually provides more incremental values of test result data.

Figure 20B:
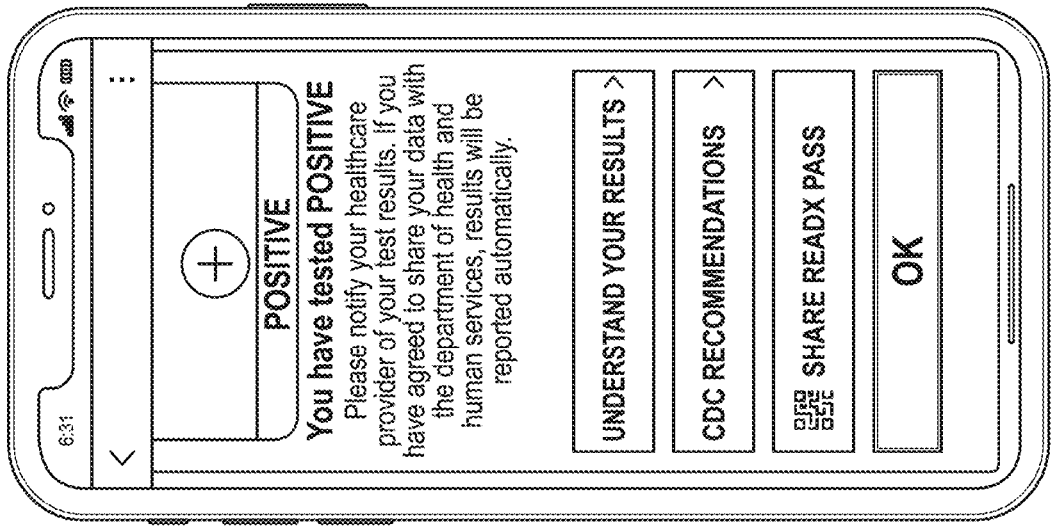
FIG. 20B illustrates a page of the rapid test results system that prompts the user to select between the virtual button options of "Understanding Your Results," "CDC Recommendations," and "Share ReaDX Pass."
Figure 20A:
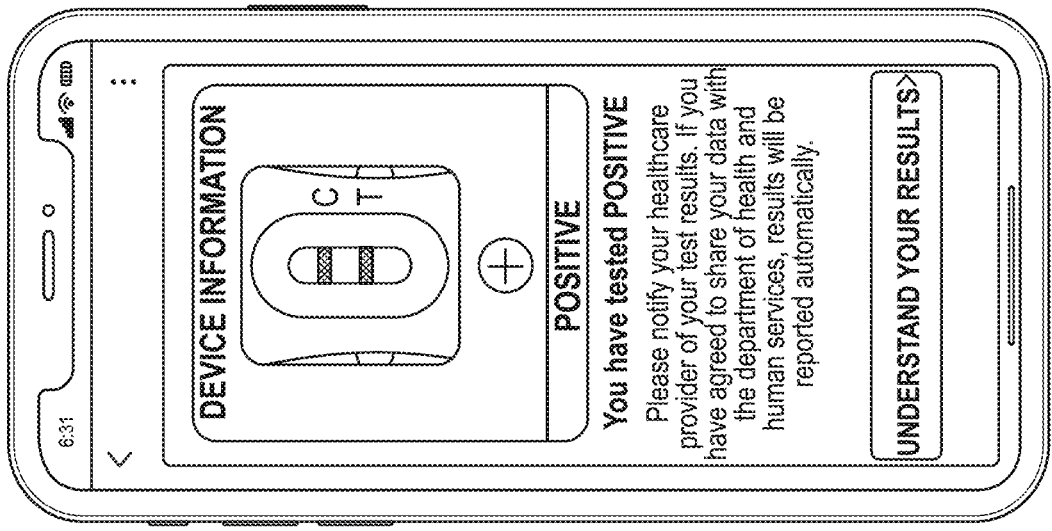
FIG. 20A illustrates a page of the rapid test results system that informs the user of the results of the test.
Figure 20D:
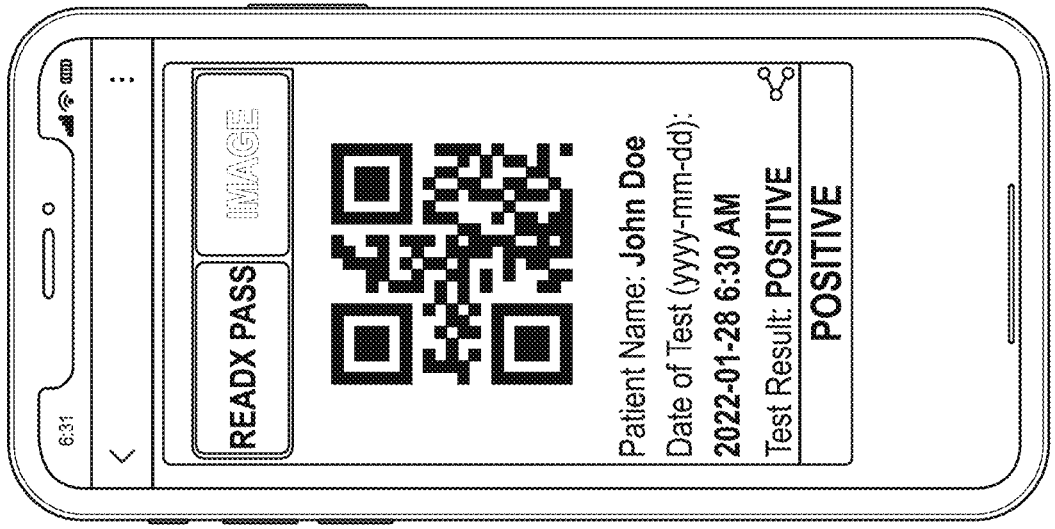
FIG. 20D illustrates a page of the rapid test results system that displays data to the user that is informative of a ReaDX Pass positive test result.
Figure 20C:
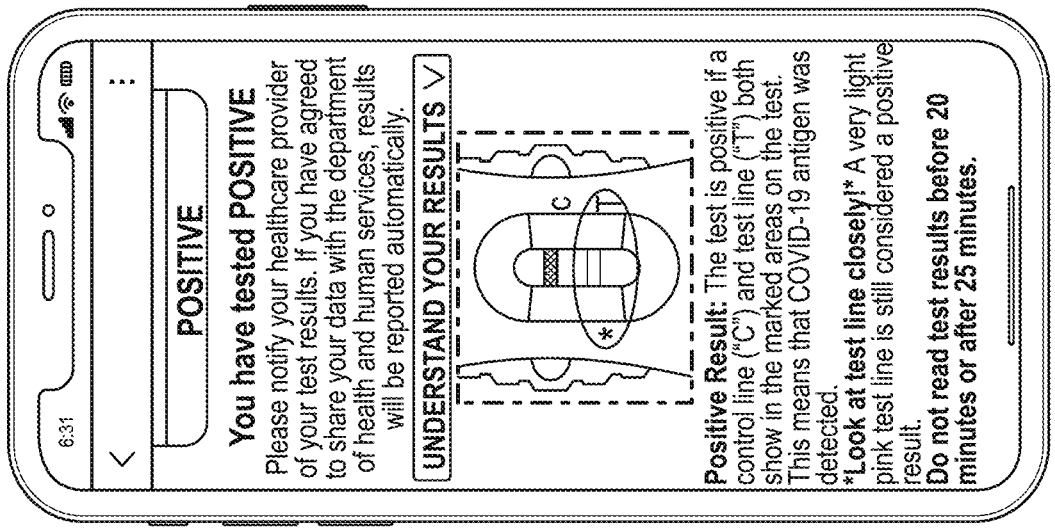
FIG. 20C illustrates a page of the rapid test results system that displays data to the user that is informative of a positive test result.
Figure 20E:
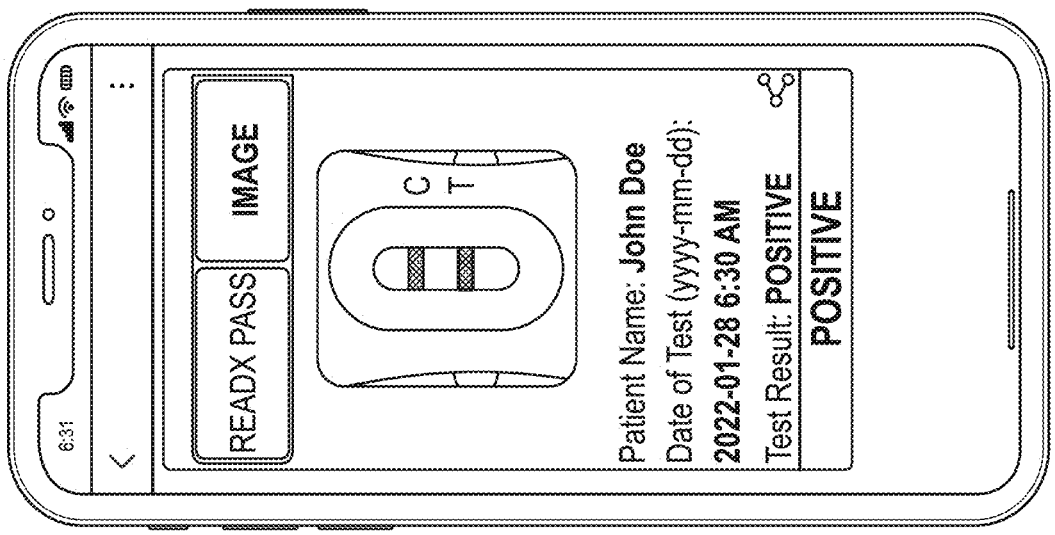
FIG. 20E illustrates a page of the rapid test results system that displays an image to the user that is informative of a ReaDX Pass positive test result.

Referring now to FIGS. 20A and 20B, this page of the rapid test results system instructs the user of the results of the test. In this sample embodiment, the user has tested positive for the particular assay (e.g., COVID-19). The user is instructed to notify the user's healthcare provider of the test results. The rapid test results system further notes that if the user has previously agreed to share the user's healthcare data with the department of health and human services, then the results will be reported automatically. At FIG. 20B, the user is prompted to select between the virtual button options of "Understanding Your Results," "CDC Recommendations," and "Share ReaDX Pass." As shown in FIG. 20C, if the user selects to "Understand Your Results" then the data that is informative of a positive test result is explained to the user. As shown in FIG. 20D, if the user selects "Share ReaDX Pass," then the code (e.g., QR code, bar code, etc.) that is informative of a ReaDX Pass positive test result is shown to the user. Additionally, as shown in FIG. 20E, if the user selects "Share ReaDX Pass" and image, then the image that represents the positive test results in the ReaDX Pass is shown to the user.

Figure 21A:
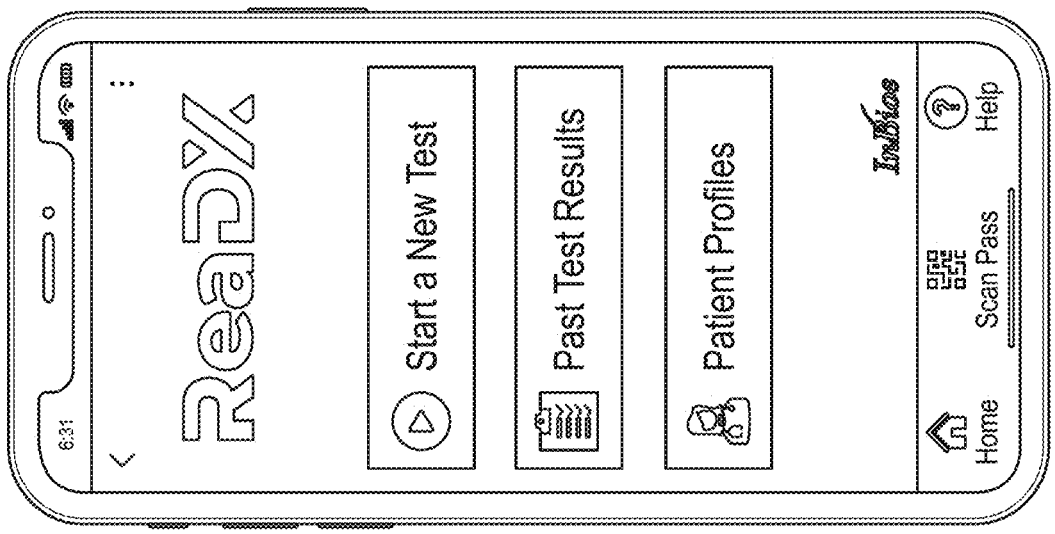
FIG. 21A illustrates a page of the rapid test results system that displays selection regions for "Start a New Test," "Past Test Results," and "Patient Profiles."
Figure 21C:
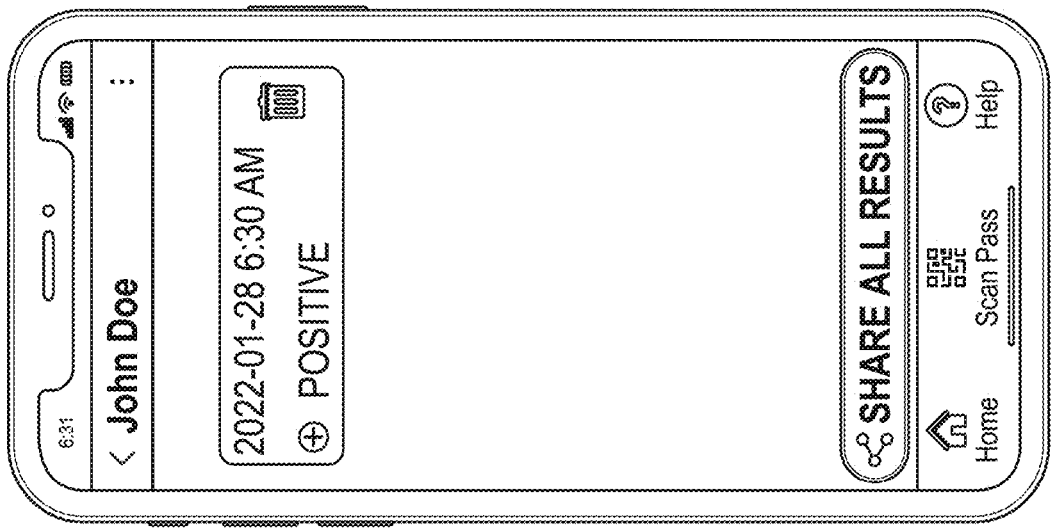
FIG. 21C illustrates a page of the rapid test results system in which the user is presented with the positive test result confirmation.
Figure 21B:
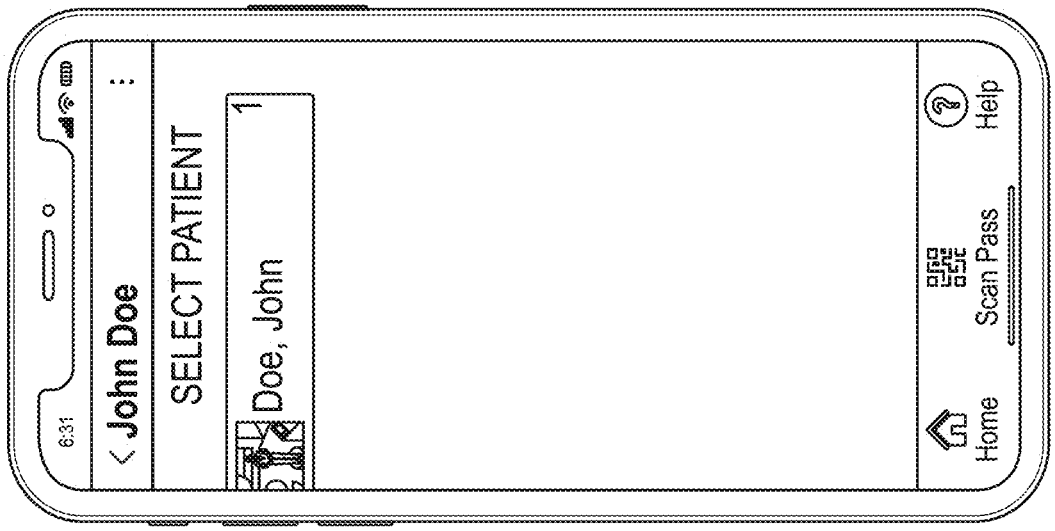
FIG. 21B illustrates a page of the rapid test results system in which the user selects the virtual button of "Patient Profiles" and is presented with the selected patient of John Doe.

As shown in FIG. 21A, in some embodiments, the rapid test results system returns to the initial page shown in FIG. 3A, with selection regions for "Start a New Test," "Past Test Results," and "Patient Profiles." In this instance, the user selects the virtual button of "Patient Profiles" and is presented with the selected patient of John Doe, as shown in FIG. 21B. In some embodiments of the rapid test results system, as shown in FIG. 21C, the user is presented with the positive test result confirmation, as well as the date and time of the positive test result, which may be important for determining information such as the length of a required quarantine. In FIG. 21C, the user is also presented with the option to share the test results.

Figure 22B:
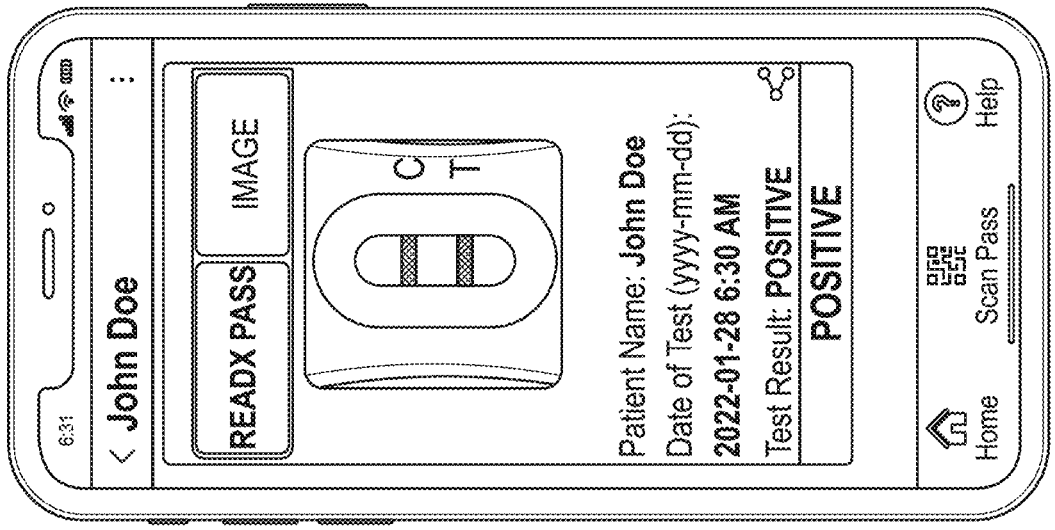
FIG. 22B illustrates a page of the rapid test results system showing the ReaDX Pass screen with the displayed positive test result image, patient name, date of test, time of test, and test result.
Figure 22A:
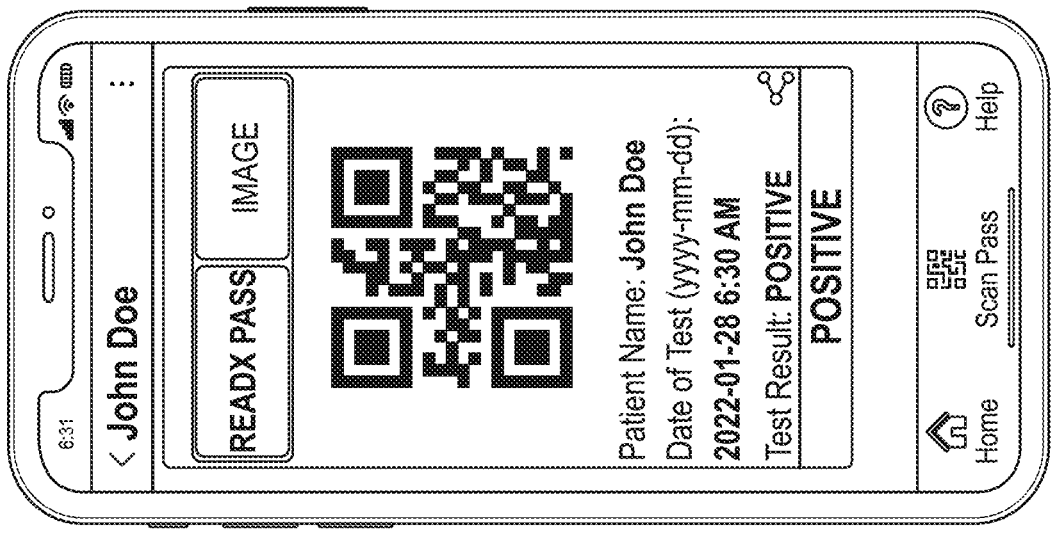
FIG. 22A illustrates a page of the rapid test results system showing the ReaDX Pass screen with the displayed QR code, patient name, date of test, time of test, and test result.

Referring now to FIG. 22A, in this embodiment the user has selected the "share test results" option and is now on the ReaDX Pass screen with the displayed QR code, patient name, date of test, time of test, and test result. Referring now to FIG. 22B, in this embodiment the user has selected the "share test results" option and the "image" virtual button. These selections cause the ReaDX Pass screen to display the positive test result image, patient name, date of test, time of test, and test result.

Figure 23:
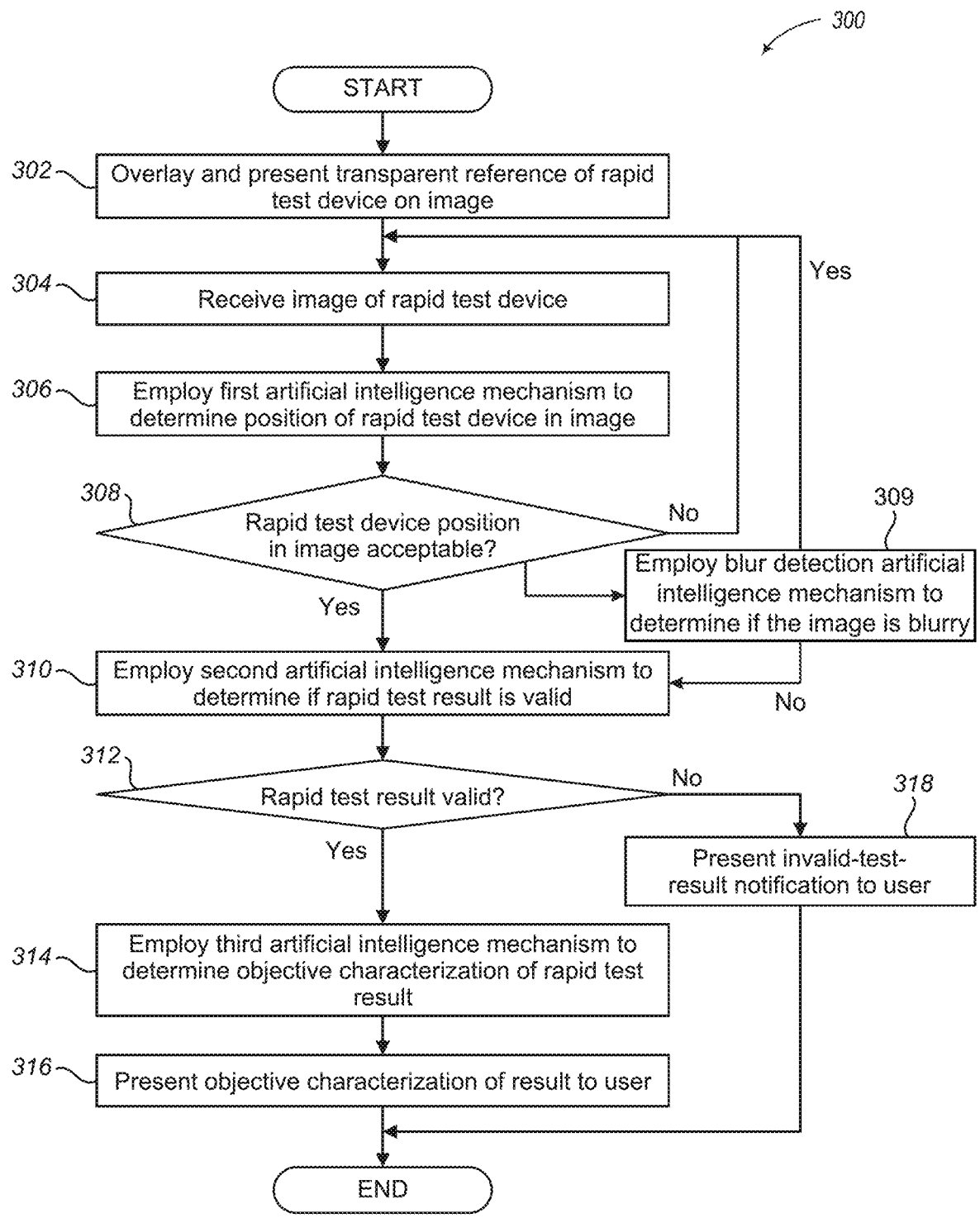
FIG. 23 illustrates a logical flow diagram showing one embodiment of a process for capturing images of a rapid test device to validate results in accordance with embodiments described herein.

The operation of certain aspects will now be described with respect to FIG. 23. In at least one of various embodiments, process 300 described in conjunction with FIG. 23 may be implemented by one or more processors or executed via circuitry on one or more computing devices, such as reader 124 or remote server 126. FIG. 23 illustrates a logical flow diagram showing one embodiment of a process 300 for capturing images of a lateral flow assay cassette 128 and employing artificial intelligence mechanisms to validate results in accordance with embodiments described herein.

In some embodiments, process 300 begins, after a start block, at block 302, where a transparent reference of a lateral flow assay cassette is presented to a user as being overlaid on images captured by the reader. In some embodiments, the overlaid image is displayed to the user via a graphical user interface. In other embodiments, the overlaid image is transmitted or sent to another computing device for display to the user.

The transparent reference is a partially transparent representation of the lateral flow assay cassette being validated and may be referred to as the lateral flow assay cassette reference. The transparent reference provides a visual cue to a user as to an ideal position for the lateral flow assay cassette to be within the images for proper processing and analysis. In other embodiments, a transparent reference is not implemented, but rather alignment bars or other alignment techniques are implemented to provide visual cues to a user.

In some embodiments, the particular type of lateral flow assay cassette reference is selected by a user. In at least one embodiment, a list of possible lateral flow assay cassette references is presented to the user. The user can then select the lateral flow assay cassette that matches or corresponds to the rapid test device being validated. In other embodiments, an artificial intelligence mechanism is employed on the received image to select the lateral flow assay cassette reference. In yet other embodiments, the artificial intelligence mechanism may be employed to determine a set of possible lateral flow assay cassette references, which is then presented to the user. The user is then prompted to select the particular lateral flow assay cassette reference of the rapid test device being validated. In some other embodiments, a machine readable symbol (e.g., barcode or QR code) or other identifying information on the lateral flow assay cassette, or the packaging of the lateral flow assay cassette, may be scanned to identify or select the lateral flow assay cassette.

In embodiments where the image includes a plurality of lateral flow assay cassettes, a plurality of lateral flow assay cassette references may be overlaid on the received image. In some embodiments, the positioning of the plurality of lateral flow assay cassette references in the overlaid image may be determined based on the positioning of lateral flow assay cassettes being validated within the received image, such as by employing a plurality of machine learning models trained to identify different lateral flow assay cassettes and their locations within an image.

Process 300 proceeds to block 304, where an image of a lateral flow assay cassette is received. In some embodiments, the image is captured by the device executing process 300, e.g., reader 124. In other embodiments, the image is captured by a device remote from the device executing process 300, e.g., remote server 126. In some embodiments, the image may include a plurality of lateral flow assay cassettes.

Process 300 continues at block 306, where a first artificial intelligence mechanism is employed to determine a position of the lateral flow assay cassette in the received image. In some embodiments, the first artificial intelligence mechanism is a machine learning model trained to identify the lateral flow assay cassette in an image. In other embodiments, the first artificial intelligence mechanism stores one or more characteristics of lateral flow assay cassettes in which to compare the received image.

Process 300 proceeds next to decision block 308, where a determination is made whether the position of the lateral flow assay cassette in the received image is acceptable. In some embodiments, the positioning of the lateral flow assay cassette in the image is acceptable when the first artificial intelligence mechanism identifies the lateral flow assay cassette in the image. In other embodiments, the position of the lateral flow assay cassette in the image is acceptable when the first artificial intelligence mechanism indicates that the lateral flow assay cassette is positioned within a selected threshold size, rotation, and tilt of the lateral flow assay cassette reference. If the position of the lateral flow assay cassette in the image is acceptable, process 300 flows to block 310; otherwise, process 300 loops to block 302 to continue to receive additional images of the lateral flow assay cassette.

In some embodiments when process 300 loops to block 302, an instruction may be presented to the user indicating advice on how to better position the lateral flow assay cassette within the image. The looping of process 300 may enable a plurality of images to be captured as a video to be displayed to the user in real time so that the user can move the physical lateral flow assay cassette (or camera) in a way to align the physical lateral flow assay cassette with the lateral flow assay cassette reference overlaid on the video. Once aligned, one or more images can be captured to be further analyzed by process 300. These images can be captured in response to manual input from the user, or they may be automatically captured when the system determines that the position of the lateral flow assay cassette relative to the camera is acceptable.

At block 309, an optional blurriness detection artificial intelligence mechanism is employed (in one or more embodiments) to determines if there is an unacceptable amount of blurriness in the captured image of the rapid test device. In some embodiments, the blurriness detection artificial intelligence mechanism is a machine learning classification model trained to classify blurry or non-blurry image output of the lateral flow assay cassette by the image capture device. In other embodiments, the blurriness detection artificial intelligence mechanism stores one or more characteristics of blurry or non-blurry images of the lateral flow assay cassette results to compare against the received image.

If it is determined by the optional blur detection artificial intelligence mechanism 211 that there is an un-acceptable amount of blurriness in the captured image, then the process returns to block 304 and receives a new image of the rapid test device (e.g., prompts the user to take a replacement image of the rapid test device). Alternatively, if it is determined by the optional blur detection artificial intelligence mechanism 211 that there is an acceptable amount of blurriness (or no blurriness) in the captured image, then the process continues to block 310 to determine test validity.

At block 310, a second artificial intelligence mechanism is employed to determine if the lateral flow assay cassette result is valid. In some embodiments, the second artificial intelligence mechanism is a machine learning model trained to classify valid or invalid results output by the lateral flow assay cassette. In other embodiments, the second artificial intelligence mechanism stores one or more characteristics of valid and invalid lateral flow assay cassette results in which to compare the received image.

In various embodiments, a plurality of second artificial intelligence mechanisms are generated for corresponding lateral flow assay cassettes of a plurality of different lateral flow assay cassettes. A particular second artificial intelligence mechanism is selected from the plurality of artificial intelligence mechanisms based on the lateral flow assay cassette selected or identified at block 304. This selected second artificial intelligence mechanism is then utilized with respect to the corresponding lateral flow assay cassette in the received image.

In some embodiments, a single lateral flow assay cassette may have multiple output areas with different results. In at least one such embodiment, different second artificial intelligence mechanisms are generated for each corresponding output area of the lateral flow assay cassette and employed on the received image to determine if results in each separate output area are valid or invalid.

Process 300 continues next at decision block 312, where a determination is made whether the lateral flow assay cassette results are valid based on the employment of the second artificial intelligence mechanism. If the test results are valid, process 300 flows to block 314; otherwise, process 300 flows to block 318 to present an invalid-test-result notification to the user via a graphical user interface. In some embodiments, the invalid-test-result notification may indicate the result "invalid." In other embodiments, the invalid-test-result notification may provide additional information indicating whether the sample was too small or tainted, or if the lateral flow assay cassette malfunctioned.

At block 314, a third artificial intelligence mechanism is employed to determine a quantitative level of the lateral flow assay cassette result. In some embodiments, the third artificial intelligence mechanism is a machine learning model trained to classify possible test results output by the lateral flow assay cassette. In other embodiments, the third artificial intelligence mechanism stores one or more characteristics of each possible test result of the lateral flow assay cassette in which to compare the received image.

For example, in one embodiment, a positive nAb test result may be a full-length control line and a full-length test line as illustrated in the left most lateral flow assay of FIG. 1B. A negative nAb test result may be a full-length control line and no test line, as illustrated in the right most lateral flow assay of FIG. 1B. In other embodiments, different objective results may be identifiable by color, intensity, alphanumeric codes, and the like.

As described herein in the context of the lateral flow assay, semi-quantitative results, such as negative, weak positive, positive, and strong positive may be calculated by the third artificial intelligence mechanism using the intensity or darkness of the test line and any of various possible calibration references, as shown in FIG. 1B. A quantitative result may also be calculated by the third artificial intelligence mechanism.

In various embodiments, a plurality of third artificial intelligence mechanisms are generated for corresponding lateral flow assay cassettes of a plurality of different lateral flow assay cassettes. A particular third artificial intelligence mechanism is selected from the plurality of artificial intelligence mechanisms based on the lateral flow assay cassette selected or identified at block 304. This selected third artificial intelligence mechanism is then utilized with respect to the corresponding lateral flow assay cassette in the received image to identify the corresponding results.

As mentioned above, a single lateral flow assay cassette may have multiple output areas with different results. In at least one embodiment, different third artificial intelligence mechanisms are generated for each corresponding output area of the lateral flow assay cassette and employed on the received image to determine the objective characterization of the results in each separate output area.

Process 300 proceeds next to block 316, where the objective characterization (e.g., quantitative level) of the assay results are presented to a user. In some embodiments, the results are displayed to the user via a graphical user interface. In other embodiments, the results are transmitted or sent to another computing device for display to the user. The displayed objective characterization may be a qualitative or binary result, such as "positive" or "negative," or it may be semi-quantitative and/or quantitative. In some embodiments, a confidence level or value of the objective characterization (e.g., quantitative level) may be determined and displayed to the user.

After block 316 or after block 318, process 300 terminates or otherwise returns to a calling process to perform other actions. In some embodiments, process 300 may loop (not illustrated) to block 302 to receive new images of a lateral flow assay cassette.

Results of a lateral flow assay cassette validated using system 100 or process 300 may, in some embodiments, be generated and displayed using a smartphone application. In these embodiments, a ratio score may be generated based on signal intensity (e.g., darkness) of the test line compared to that of the control line. The ratio or another quantification based on it may be displayed to the user. Alternatively, or in addition, a cut-off ratio for the type of assay may be generated using a receiver operating characteristic curve from a panel of negative and positive samples. Ratios may be correlated with semi-quantitative values using a panel of known nAbs. A code may be supplied with each lateral flow assay cassette that provides adjustments to be made to the base cut-off ratio and semi-quantitative values, as well as possible adjustments to quantitative values to ensure uniformity across assays. The adjustments associated with the code are determined by testing of representative lateral flow assay cassettes from batches prior to shipment to users.

Results may also be shared with others in a secure and verifiable fashion. For example, the smartphone application used to validate the results of a lateral flow assay cassette may generate a QR code or other digital code associated with the results. This code may be displayed on the smartphone and scanned by another smartphone or reader or it may be transmitted to another smartphone or reader. The QR code may be opened in the same or a compatible application on the other smartphone or reader and may display information regarding the lateral flow assay cassette validation results. For example, it may display information about the patient, date of assay, and positive/negative, semi-quantitative, or quantitative results.

Lateral flow assays of the present disclosure, particularly in conjunction with artificial intelligence-based readers as disclosed herein, may be readily usable by patients at home or by medical personnel in a point-of-care or field setting and may provide easy transmission and verification of neutralizing antibody status for SARS-CoV-2 or any of a range of infectious agents.

In some embodiments, the present disclosure further provides a kit for detection of nAbs in a sample from a patient. The kit includes a viral receptor-binding protein-label complex and a target protein. Kits may further include sample preparation materials, such as buffers and diluents, and/or sample collection materials, such as lancets and/or swabs or capillary tubes.

For lateral flow cassette-based detection, the kit may further include a lateral flow assay cassette as described herein that has at least a test line, a control line, and materials sufficient to cause results to be presented using the test line and control line. The lateral flow assay cassette may further include a chase buffer, instructions for use, a code or instructions for downloading a reader application, and/or a digital or readable label identifying the assay or lot.

Figure 24:
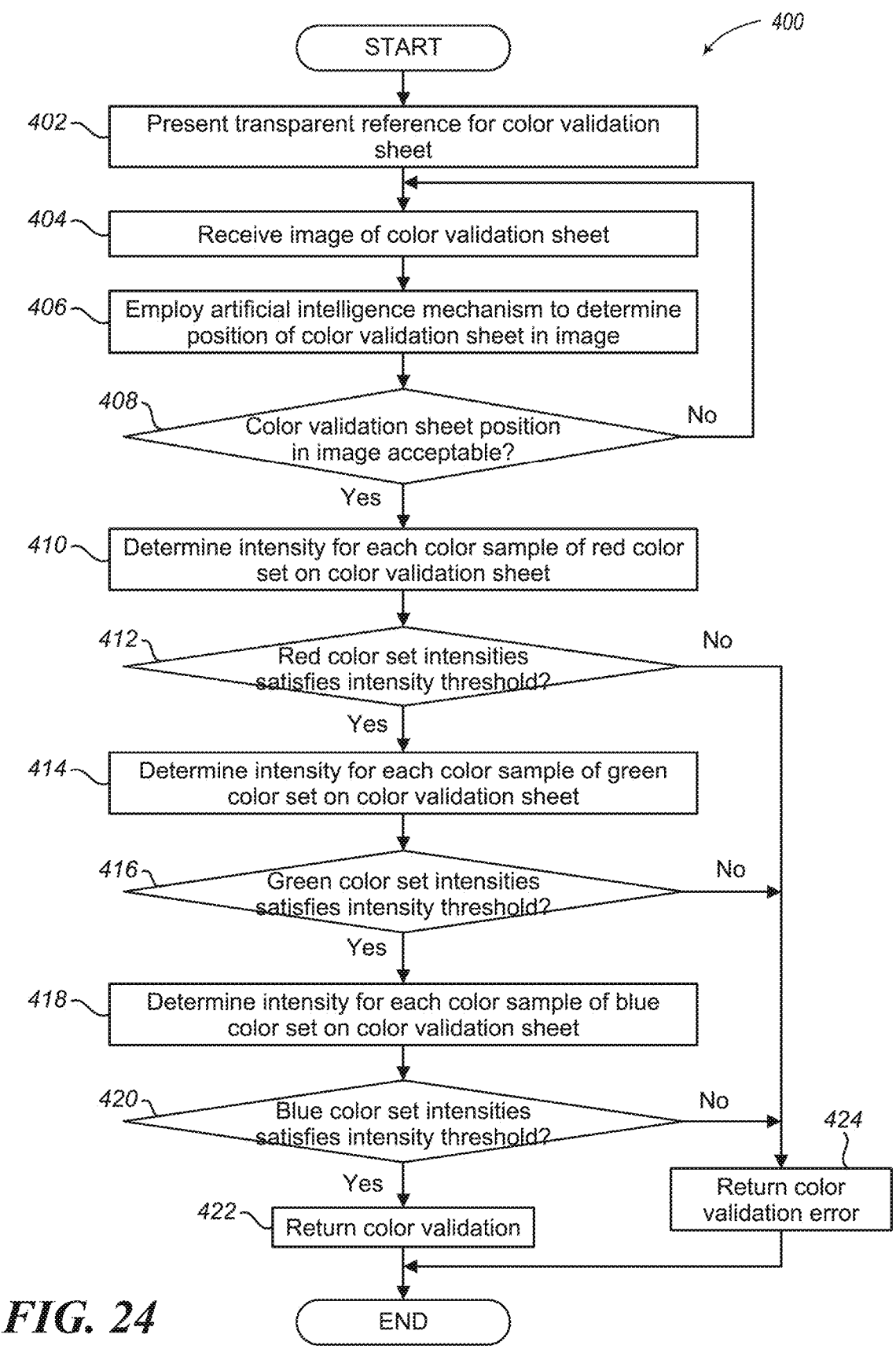
FIG. 24 illustrates a logical flow diagram showing one embodiment of a process for capturing images of a color validation sheet and employing artificial intelligence mechanisms to validate camera colors in accordance with embodiments described herein.

FIG. 24 illustrates a logical flow diagram showing one embodiment of a process 400 for capturing images of a color validation sheet and employing artificial intelligence mechanisms to validate camera colors in accordance with embodiments described herein.

In some embodiments, a user may select or input a request to perform the color validation process. In other embodiments, the color validation process may be automatically requested at select or predetermined times, such as prior to the first analysis of a rapid test device, after a threshold number of rapid test devices have been analyzed, when a user selects a new type of rapid test device, after a select amount of time has lapsed, etc. In yet other embodiments, the color validation process may be automatically performed in response to detection of a threshold image condition during the analysis of a rapid test device. For example, if a rapid test device is a known color, but a different color is detected in an initial image or in a plurality of images, such as images captured at block 302 in FIG. 23, then the color validation process may commence. In these situations, the lighting—such as low-light conditions, utilization of red lighting or other non-white lighting, and the like—may impact the accuracy of one or more of the artificial intelligence mechanisms employed in process 300 in FIG. 23. Accordingly, the color validation process may be employed to determine if the lighting has the potential to impact the analysis of a rapid test device.

Process 400 begins, after a start block, at block 402, where a transparent reference of a color validation sheet is presented to a user as being overlaid on images captured by the rapid-test-validation computing device. In some embodiments, the overlaid image is displayed to the user via a graphical user interface. In other embodiments, the overlaid images are transmitted or sent to another computing device for display to the user.

In some embodiments, the transparent reference is an alignment frame, but contains no other visual representations of a color validation sheet. In other embodiments, the transparent reference is a partially transparent representation of the color validation sheet. The transparent reference provides a visual cue to a user as to an ideal position for the color validation sheet to be within the image for proper processing and analysis.

Process 400 proceeds to block 404, where an image of a color validation sheet is received. In some embodiments, the image is captured by the device executing process 300 in FIG. 24, e.g., rapid-test-validation computing device 124. The color validation sheet includes a plurality of different color samples having different intensities. In at least one embodiment, the color validation sheet includes seven color samples of different intensities for a plurality of different colors, such as red, green, and blue. Accordingly, the color validation sheet includes seven red color samples, seven green color samples, and seven blue colors samples, where each sample of each color has a different intensity. Other colors and numbers of color samples may also be utilized.

An example of a color validation sheet is shown in FIG. 24. Although FIG. 24 is in grayscale, the left-most column may be red, the center column may be green, and the right column may be blue, where the top row includes the highest intensity colors, the bottom row includes the lowest intensity colors, and the rows between the top and bottom include degrading intensity colors from top to bottom. This example arrangement of colors and intensities is not limiting, and other embodiments could have different arrangements of colors and intensities. Additional details are discussed below in conjunction with FIG. 24.

Process 400 continues at block 406, where an artificial intelligence mechanism is employed to determine a position of the color validation sheet in the received image. In some embodiments, the artificial intelligence mechanism is a machine learning model trained to identify the color validation sheet in an image. In other embodiments, the artificial intelligence mechanism stores one or more characteristics of the color validation sheet to compare with the received image. In yet other embodiments, an object tracking mechanism may be employed to detect a position of the color validation sheet in the image relative to the transparent reference or alignment frame.

Process 400 proceeds next to decision block 408, where a determination is made whether the position of the color validation sheet in the received image is acceptable. In some embodiments, the positioning of the color validation sheet in the image is acceptable when the artificial intelligence mechanism identifies the color validation sheet in the image. In other embodiments, the position of the color validation sheet in the image is acceptable when the artificial intelligence mechanism indicates that the color validation sheet is positioned within a selected threshold size, rotation, or tilt relative to the transparent reference. If the position of the color validation sheet in the image is acceptable, process 400 flows to block 410; otherwise, process 400 loops to block 402 to continue to receive additional images of the color validation sheet.

In some embodiments when process 400 loops to block 402, an instruction may be presented to the user indicating advice on how to better position the color validation sheet within the image. The looping of process 400 may enable a plurality of images to be captured as a video to be displayed to the user in real time so that the user can move the physical color validation sheet (or camera) in a way to align the physical color validation sheet with the transparent reference or alignment frame overlaid on the video. Once aligned, one or more images can be captured to be further analyzed by process 400. These images can be captured in response to manual input from the user, or they may be automatically captured when the system determines that the position of the color validation sheet relative to the camera is acceptable.

At block 410, an intensity of each of a plurality of color samples of a red color set on the color validation sheet is determined. As mentioned above, the color validation sheet includes a plurality of different color samples, each having a different intensity, for multiple colors. In at least one embodiment, the color validation sheet includes seven different red sample intensities. The intensity of each of these sample colors is calculated.

Process 400 proceeds next to decision block 412, where a determination is made whether the intensities for the red color set satisfy one or more intensity thresholds. In some embodiments, each sample color in the red color set corresponds to a separate intensity threshold. Each corresponding threshold may be a single intensity value, a range of intensity values, or an intensity value with a tolerance level. In this way, each separate calculated color sample intensity is compared to the corresponding threshold for that color sample. In some embodiments, the intensity threshold is satisfied if each separate color sample intensity threshold is satisfied. In other embodiments, the intensity threshold is satisfied if a select number of color sample intensity thresholds are satisfied.

In other embodiments, the intensity threshold may be a comparison between the different color sample intensities. In one embodiment, the comparison may be between the highest calculated intensity and the lowest calculated intensity. If the difference between these calculated intensities is above a threshold amount (e.g., 0.3), then the intensity threshold is satisfied. In another embodiment, the comparison may be between each calculated intensity to determine if there is a sequential increase from one calculated intensity to the next from the lowest calculated intensity to the highest calculated intensity. The order of color sample intensities for this sequential increase is determined by the order of color samples on the color validation sheet.

In various embodiments, one or more of these or other thresholds may be utilized to determine if the red color set intensity satisfies the intensity threshold. For example, the intensity threshold may be satisfied if the color sample intensities sequentially increase and the difference between the lowest calculated intensity and the highest calculated intensity exceeds a select value.

If the red color set intensities satisfy the one or more intensity thresholds, then process 400 flows to block 414; otherwise, process 400 flows to block 424. At block 414, an intensity of each of a plurality of color samples of a green color set on the color validation sheet is determined. In at least one embodiment, the color validation sheet includes seven different green sample intensities. The intensity of each of these sample colors is calculated.

Process 400 proceeds next to decision block 416, where a determination is made whether the intensities for the green color set satisfy one or more intensity thresholds. In various embodiments, decision block 416 may employ embodiments similar to block 414, but for the green color set. In some embodiments, the thresholds employed for the red color set may be the same for the green color set. In other embodiments, the thresholds may be modified or customized for the green color set. If the green color set intensities satisfy the one or more intensity thresholds, then process 400 flows to block 418; otherwise, process 400 flows to block 424.

At block 418, an intensity of each of a plurality of color samples of a blue color set on the color validation sheet is determined. In at least one embodiment, the color validation sheet includes seven different blue sample intensities. The intensity of each of these sample colors is calculated.

Process 400 proceeds next to decision block 420 where a determination is made whether the intensities for the blue color set satisfy one or more intensity thresholds. In various embodiments, decision block 420 may employ embodiments similar to block 414, but for the blue color set. In some embodiments, the thresholds employed for the red and green color sets may be the same for the blue color set. In other embodiments, the thresholds may be modified or customized for the blue color set. If the blue color set intensities satisfy the one or more intensity thresholds, then process 400 flows to block 422; otherwise, process 400 flows to block 424.

At block 422, an indication that the color is valid is returned. In at least one embodiment, the satisfied color validation may automatically begin or continue process 300 in FIG. 23. In other embodiments, the user is notified that the color validation process was successful. After block 422, process 400 may terminate or otherwise return to a calling process to perform other actions.

If, at decision blocks 412, 416, or 420, an intensity threshold is not satisfied, then process 400 flows from these decision blocks to block 424. At block 424, an indication that the color is invalid or a color validation error is returned. In some embodiments, the user is notified that the color validation process was unsuccessful. After block 424, process 400 may terminate or otherwise return to a calling process to perform other actions.

Although process 400 describes a processing of red, green, and blue color sets, embodiments are not so limited. In some embodiments, only a single color may be analyzed, two colors may be analyzed or a plurality of colors may be analyzed to determine if one or more intensity thresholds are satisfied. Moreover, other colors or numbers of color samples may also be utilized. In some embodiments, the image of the color validation sheet is converted into a grayscale image prior to calculating the color intensities.

FIGS. 25A-25D illustrate use case examples of graphical user interfaces presenting information to a user with respect to validating rapid test device results in accordance with embodiments described herein. In various embodiments, graphical user interfaces 500A-500D of FIGS. 25A-25D, respectively, may be presented on a rapid-test-validation computing device 124 of FIG. 1A.

Figures 25A, 25B:
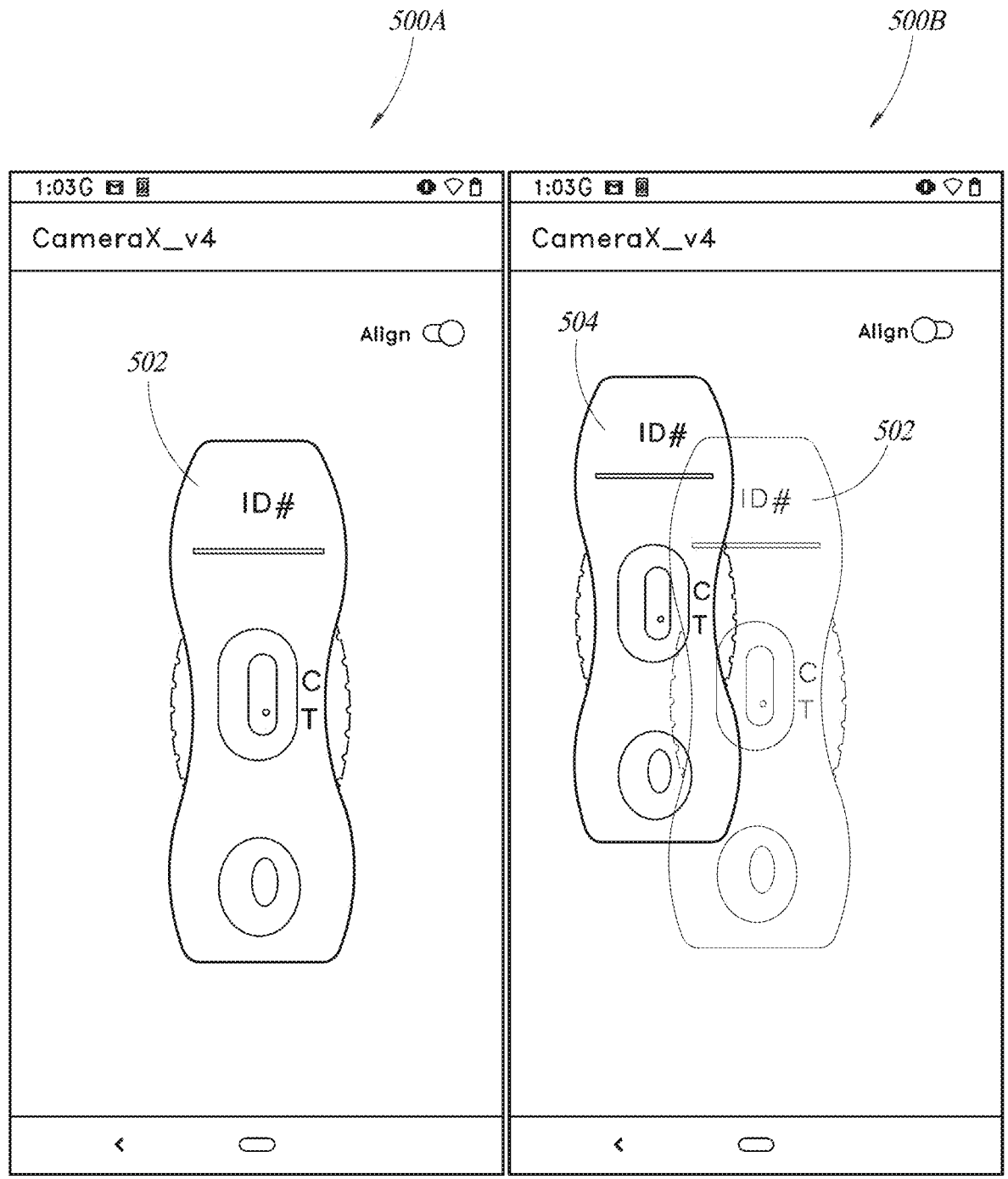

FIG. 25A illustrates a use case example of a graphical user interface 500A displaying an image having a rapid-test-device reference 502 overlaid on the received image. In this example, there is no physical rapid test device present in the presented image, such as before an image of a rapid test device is captured. As can be seen, the rapid-test-device reference 502 is a semi-transparent representation of a rapid test device superimposed on the image that is displayed to the user.

FIG. 25B illustrates a use case example of a graphical user interface 500B displaying an image having a physical or actual rapid test device 504 and a rapid-test-device reference 502 overlaid on the received image. In this example, the rapid test device 504 does not align with the rapid-test-device reference 502. Overlaying the rapid-test-device reference 502 on the image provides a guide that enables a user to move the rapid-test-validation computing device 124 into an acceptable position within the image wherein the actual rapid test device 504 is substantially aligned with the rapid-test-device reference 502 for the corresponding artificial intelligence mechanisms to be employed, as described herein.

FIG. 25C illustrates a use case example of a graphical user interface 500C displaying an output indicating that the test results 510 of the rapid test device 504 are invalid. Although not illustrated, in some embodiments, the graphical user interface 500C may display one or more notifications indicating possible reasons why the results are not valid.

FIG. 25D illustrates a use case example of a graphical user interface 500D displaying an output indicating an objective characterization (e.g., quantitative level) of the test results 512 of the rapid test device 504. In this example, the graphical user interface 500D indicates that the test results 512 are "negative." Although not illustrated, in some embodiments, the graphical user interface 500D may display one or more notifications indicating what the particular results mean. For example, if the rapid test device outputs a plurality of results, the graphical user interface may display an objective characterization of each individual output and a cumulative result from the combination of all results.

Figure 26A:
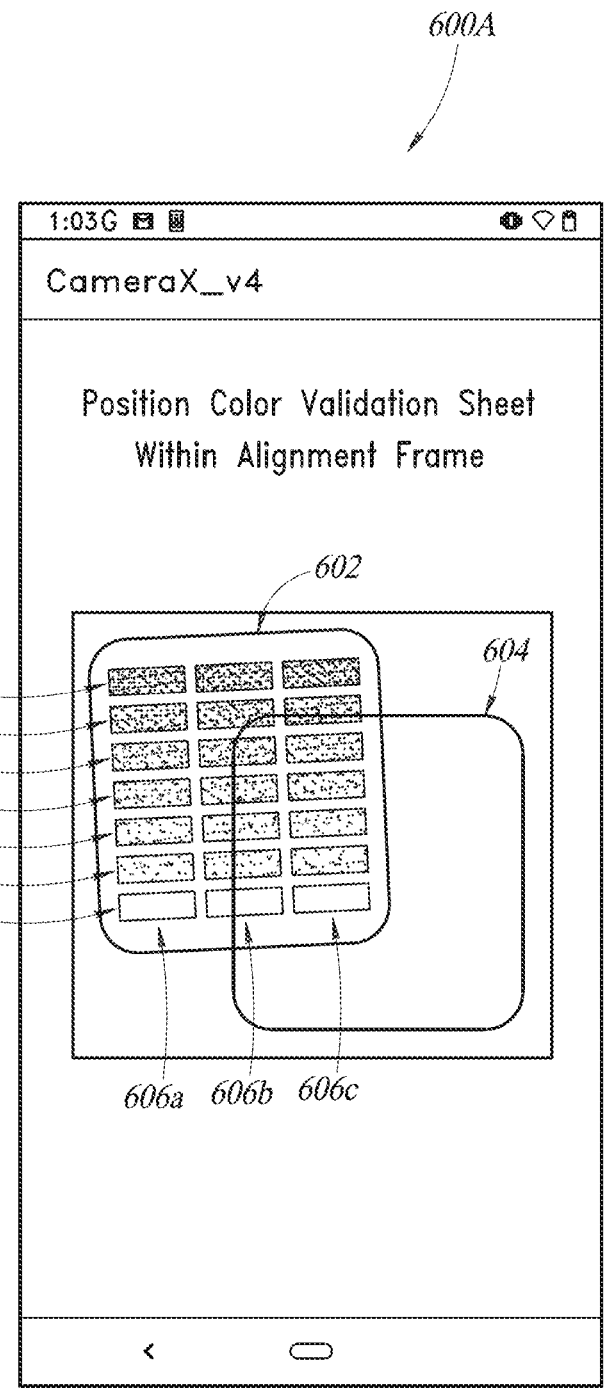
FIGS. 26A-26B illustrate use case examples of graphical user interfaces presenting information to a user with respect to validating camera colors prior to validating rapid test device results in accordance with embodiments described herein.
Figure 26B:
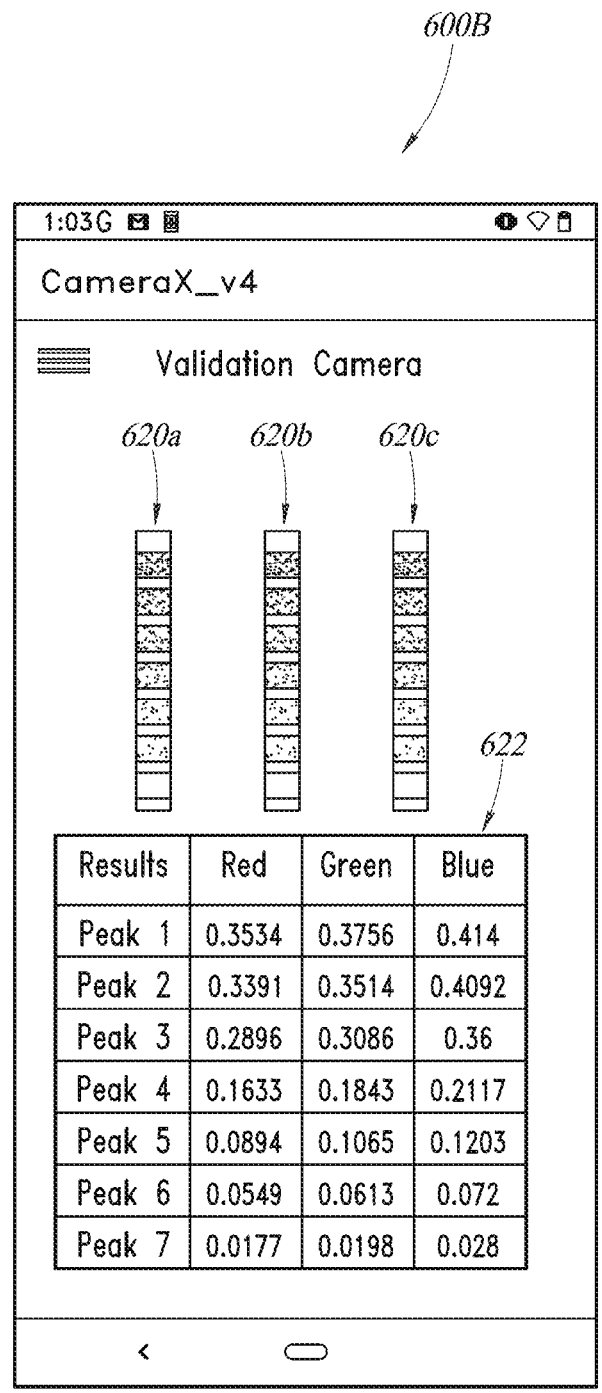

FIGS. 26A-26B illustrate use case examples of graphical user interfaces presenting information to a user with respect to validating camera colors prior to validating rapid test device results in accordance with embodiments described herein.

FIG. 26A illustrates a use case example of a graphical user interface 600A displaying an image having a physical or actual color validation sheet 602 and an alignment frame 604 overlaid on the received image. In this example, the color validation sheet 602 does not align with the alignment frame 604. Overlaying the alignment frame 604 on the image provides a guide that enables a user to move the rapid-test-validation computing device 124 or the color validation sheet 602 into an acceptable position within the image wherein the actual color validation sheet is substantially aligned with the alignment frame 604 for the corresponding artificial intelligence mechanisms to be employed, as described herein.

In this example, the color validation sheet 602 includes three color sample sets 606a-606c. Color sample set 606a is a red set that includes a plurality of different intensity samples 608a-608g. Sample 608a has the lowest red intensity and sample 608g has the highest red intensity for the set. The intensity of the samples 608a-608g sequentially increase from sample 608a to sample 608g. Color sample set 606b is a green set and color sample set 606c is a blue set, which both include a plurality of different intensity samples that sequentially increase from a lowest intensity to a highest intensity for each respective set (these samples are not individually referenced for clarity of the figure).

FIG. 26B illustrates a use case example of a graphical user interface 600B displaying results of the processing of the color samples from the color validation sheet 602 in FIG. 26A. Outputs 620a-620c illustrate grayscale intensities of the color samples determined from the color validation sheet 602. For example, output 620a is the grayscale intensities for the red color set 606a, output 620b is the grayscale intensities for the green color set 606b, and output 620c is the grayscale intensities for the blue color set 606c. The numerical values of these intensities is shown in table 622, which can be used to determine if the calculated intensities satisfy one or more intensity thresholds, as described herein. In some embodiments, the system may not display the numerical values of the determined intensities. Rather, in some embodiments, the system may display a "pass/fail" result without providing additional details as to the determined intensities. The use of the color validation sheet enables the system to confirm that the camera is capturing images with colors having sufficient dynamic range to properly analyze rapid test devices, as described herein.

Figure 27:
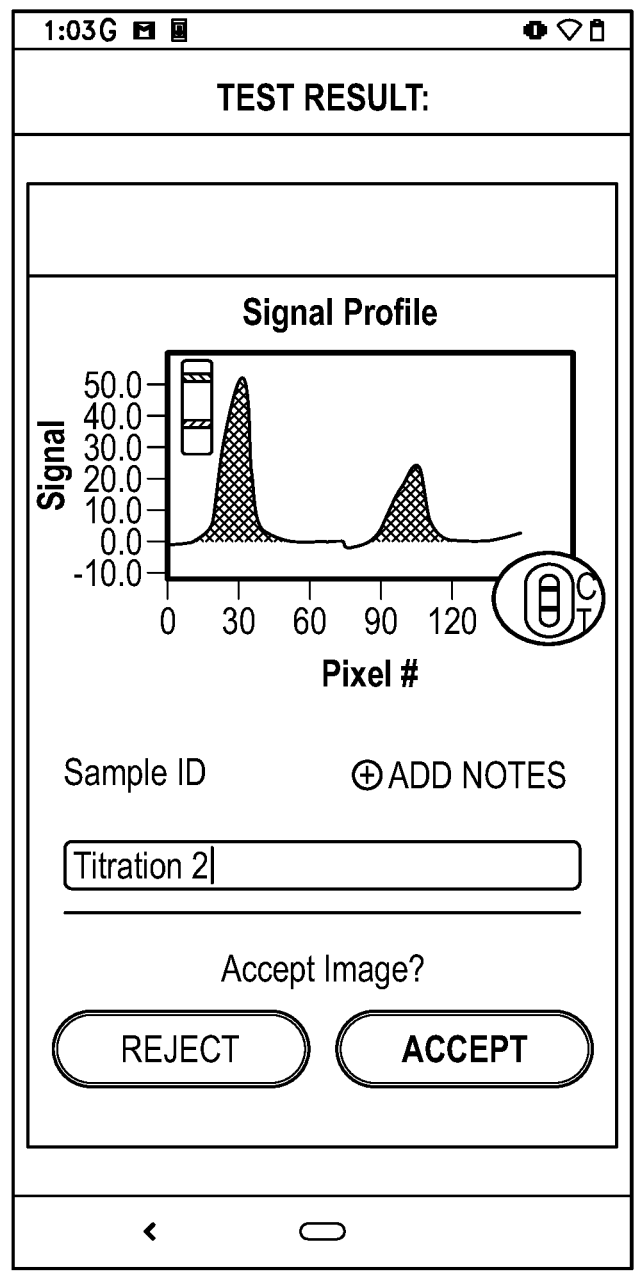
FIG. 27 depicts an example lateral flow assay cassette result displayed on a smartphone app in which the test line (right peak) has a reduced signal intensity relative to the control line (left peak).

FIG. 27 depicts an example lateral flow assay cassette result displayed on a smartphone application in which the test line (right peak) has a reduced signal intensity relative to the control line (left peak). The gray scale intensity of the test and control line areas are analytically determined and presented to the end user. In one or more such embodiments, a smartphone application captures and analyzes the read-out for the presence of nAbs as strong, moderate or weak positive, or negative. Gold-labeled control antibodies preferentially bind to target immobilized in the control region (C). Control line signal intensity measures validity and consistency from test to test. Total time to test result is 20-30 minutes. In some embodiments, test kits include single-use disposable lateral flow assay cassettes, all reagents needed for the assay, standards to calculate a standard curve, and positive and negative controls.

The smartphone application reader acquires an image of each lateral flow assay cassette and provides a semi-quantitative analysis of results. Machine learning (e.g., artificial intelligence) algorithms confirm that the user has scanned the correct test and aligned and properly centered the image. A bar/QR code uniquely identifies each kit lot. The smartphone application automatically acquires and aligns the image and interprets the results using a set of assay-specific machine learning models. The smartphone application generates a ratio score (LFE) based on the signal intensity ratio of the test: control line (T:C) and assigns a cut-off LFE value and range for each outcome (i.e., negative, weak positive, moderate positive, strong positive). Using the code for each kit lot, it mitigates lot-to-lot variability by adjusting the cut-off LFE value and range according to calibrators and standards used to qualify each batch of tests, without operator intervention. The cut-off LFE is determined by generating a receiver operating characteristic ROC curve from a panel of negative and positive samples. The cut-off LFE is established for each cassette lot and stored in a remote database for use by a reader and artificial intelligence, such as a smartphone, to apply correct thresholds for each lot.

Referring now to FIG. 28, representative images are depicted that capture images by a smartphone application of SARS-CoV-2 lateral flow neutralizing antibody (NAb) assay cassettes according to the present disclosure along with PRNT titers, LFE values, and interpreted results. Representative images of the visual results, along with PRNT titers, are also shown in FIG. 28. The use of a smartphone application or other AI-assisted reader removes ambiguity in categorizing the rapid assay results.

Sample size was also evaluated to arrive at a recommended sample volume for the SARS-CoV-2 nAb lateral flow assay. Four samples (Pre-Covid normal human serum, qPCR-confirmed naturally Covid-infected human serum, and serum from a SCoV-2 fully vaccinated (Moderna) individual diluted 1:5 in a pre-Covid serum) were tested at different loading volumes (10, 20, and 50 µl). Among samples containing anti-SCoV-2 NAbs, LFEs varied minimally among sample volumes. However, for the Pre-Covid NHS sample, the signal increased with increased sample volume, which dramatically enhanced signal intensity separation between positive and negative samples. Thus, larger sample volumes improved sensitivity for detecting weakly positive samples. This improved sensitivity is shown in FIG. 28, which shows a negative result, a weak positive result, a moderate positive result, and a strong positive result.

FIG. 28 displays images that are specifically for the NAb assay which is a competitive assay format. This competitive assay format may be quantified using the smartphone app. In this format, a "Strong Positive" result is displayed as no test line or very faint test line, while the "Negative" result is the one where there is a strong test line present. Notably, the test line signal strength is inverted when compared to typical lateral flow assay format (as shown in FIG. 1B).

Sources of assay variability include the reagents, assembly/lamination, operator-to-operator variability, and the type of device used to run the smartphone application reader. However, device-to-device variability using three Android devices (e.g., OnePlus, Pixel 4a, Moto G7, and their updated versions), and the T:C/LFE ratios were consistent and appropriately scaled the signal intensity with the different camera types.

Figure 29:
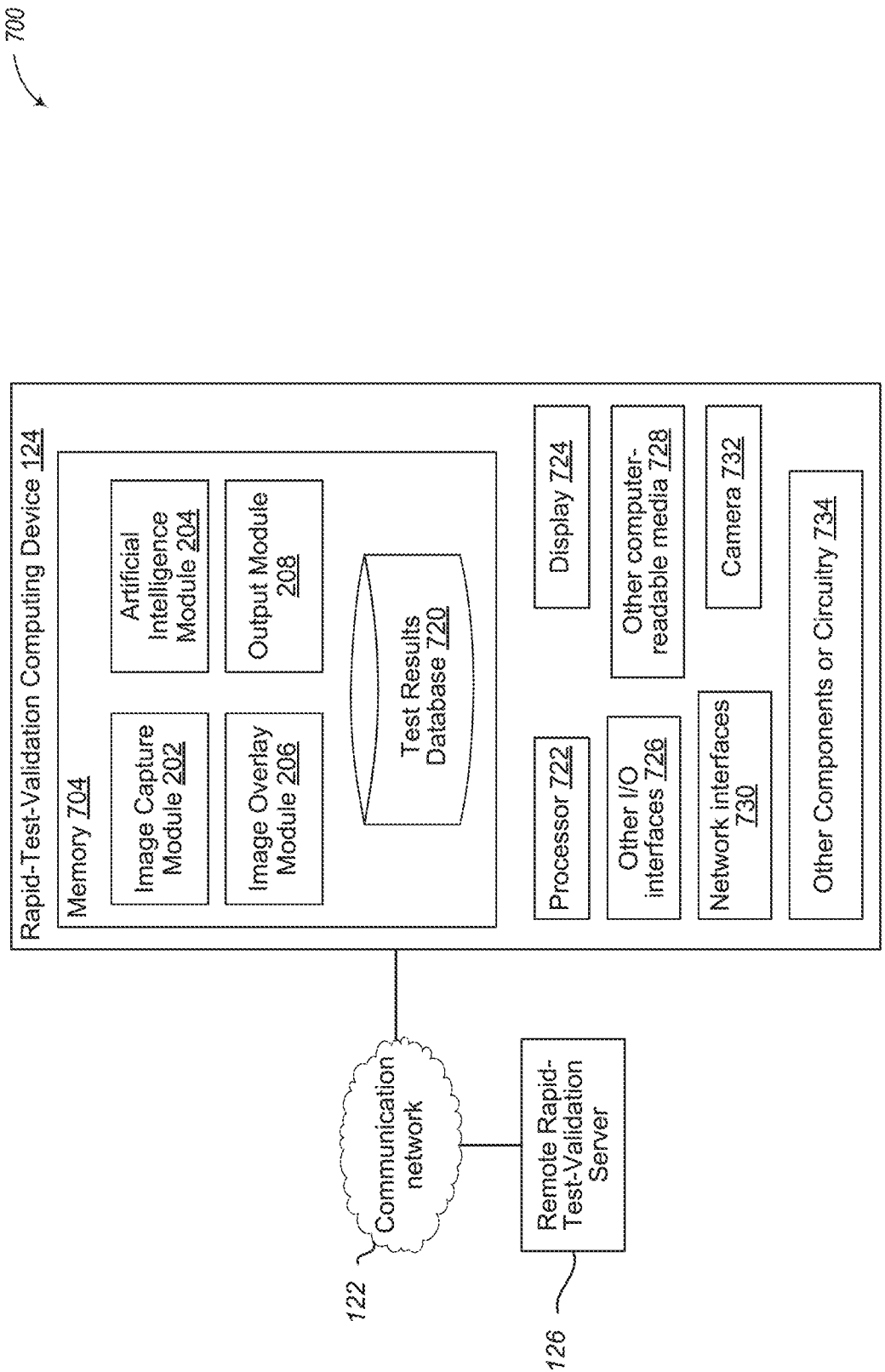
FIG. 29 shows a system diagram that describes various implementations of computing systems for implementing embodiments described herein.

FIG. 29 shows a system diagram that describes various implementations of computing systems for implementing embodiments described herein. System 700 includes rapid-test-validation computing device 124, and optionally remote rapid-test-validation server 126, similar to what is described in FIG. 1A.

As described herein, the rapid-test-validation computing device 124 is a computing device that captures images of rapid test devices, employs a first artificial intelligence mechanism to determine a position of the rapid test device in the images, optionally employs an optional blurriness detection artificial intelligence mechanism to determine if the captured imaged of the test results of the rapid test device are blurry; employs a second artificial intelligence mechanism to determine if the test results of the rapid test device are valid, and employs a third artificial intelligence mechanism to identify the test results of the rapid test device. In some embodiments, the rapid-test-validation computing device 124 captures images of a color validation sheet to determine if the colors captured by a camera of the rapid-test-validation computing device 124 are sufficient for processing images of rapid test devices. One or more special-purpose computing systems may be used to implement rapid-test-validation computing device 124. Accordingly, various embodiments described herein may be implemented in software, hardware, firmware, or in some combination thereof. The rapid-test-validation computing device 124 includes memory 704, one or more processors 722, display 724, input/output (I/O) interfaces 726, other computer-readable media 728, network interface 730, camera 732, and other components or circuitry 734.

Processor 722 includes one or more processing devices that execute computer instructions to perform actions, including at least some embodiments described herein. In various embodiments, the processor 722 may include one or more central processing units ("CPU"), programmable logic, or other processing circuitry.

Memory 704 may include one or more various types of non-volatile and/or volatile storage technologies. Examples of memory 704 may include, but are not limited to, flash memory, hard disk drives, optical drives, solid-state drives, various types of random access memory (RAM), various types of read-only memory (ROM), other computer-readable storage media (also referred to as processor-readable storage media), or the like, or any combination thereof. Memory 704 may be utilized to store information, including computer-readable instructions that are utilized by processor 722 to perform actions, including at least some embodiments described herein.

Memory 704 may have stored thereon various modules, such as image capture module 202, artificial intelligence module 204, image overlay module 206, and output module 208. The image capture module 202 captures images of one or more rapid test devices using camera 732. The camera 732 includes one or more cameras that are configured to capture images of one or more rapid test devices.

The image overlay module 206 modifies the captured images to overlay a rapid-test-device reference on the images, which may include employing an artificial intelligence mechanism to identify rapid test devices included in the captured images. The artificial intelligence module 204 employs a plurality of artificial intelligence mechanisms to determine a position of the rapid test device in the image, determine if a test result of the rapid test device is valid, and to determine an objective characterization of the test results. The output module 208 presents the modified images, validation results, and the objective characterization of the test results to a user of the rapid-test-validation computing device 124.

The memory 704 may also store test results database 720, which includes configuration information for each employed artificial intelligence mechanism, test results, rapid test device information, and the like.

The display device 724 may include one or more LCD screens, LEDs or other lights, or other types of display devices that present graphical user interfaces of information to a user (e.g., rapid-test-device reference overlaid images, validation results, test results, etc.). The other I/O interfaces 726 may include interfaces for various other input or output devices, such as audio interfaces, video interfaces, USB interfaces, physical buttons, keyboards, or the like.

The other computer-readable media 728 may include other types of stationary or removable computer-readable media, such as removable flash drives, external hard drives, or the like. The network interfaces 730 are configured to communicate with other computing devices, such as the remote rapid-test-validation server 126. Network interfaces 730 include transmitters and receivers (not illustrated) to send and receive data as described herein.

The other components or circuitry 734 may include other computing components, application-specific integrated circuits (ASICs), digital signal processors, discrete circuitry, logic gates, standard integrated circuits, controllers (e.g., by executing appropriate computing instructions, and including microcontrollers or embedded controllers), field-programmable gate arrays (FPGAs), complex programmable logic devices (CPLDs), etc., that can employ at least some embodiments described herein.

The remote rapid-test-validation server 126 includes a special-purpose computing system that may be used to communicate with the rapid-test-validation computing device 124 to provide at least some embodiments described herein. The remote rapid-test-validation server 126 may receive images from and provide results to the rapid-test-validation computing device 124 via communication network 122 in accordance with embodiments described herein. Accordingly, in some embodiments, the remote rapid-test-validation server 126 includes computing components similar to those of the rapid-test-validation computing device 124 such that various embodiments described herein may be implemented in software, hardware, firmware, or in some combination thereof.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A rapid test results imaging method, the method comprising:
obtaining one or more first images of a rapid test device using an image capture system with a display screen;
presenting the one or more images to a user on the display screen with alignment bars as the one or more first images are being obtained;
determining a position of the rapid test device in the one or more first images relative to the alignment bars;
in responsive to determining that the position of the rapid test device relative to the alignment bars is not in an acceptable range, prompting the user of the image capture system to reposition the image capture system with respect to the alignment bars;
determining, via a tilt detection system of the image capture system, a tilt angle of the image capture system relative to horizontal;
in responsive to determining that the tilt angle of the image capture system relative to horizontal is not in an acceptable range, prompting the user of the image capture system to rotate the image capture system relative to horizontal;
responsive to the position of the rapid test device being in an acceptable range relative to the alignment bars in at least one of the one or more first images, and responsive to the tilt angle of the image capture system being in an acceptable range relative to horizontal:
capturing one or more second images of the rapid test device;
determining when a result of the rapid test device is valid;
presenting an invalid-test-result notification to the user when the result of the rapid test device is invalid;
determining a quantitative level of the result of the rapid test device when the result of the rapid test device is valid; and
presenting the quantitative level of the result to the user.

2. The method of claim 1, wherein the tilt detection system uses an accelerometer and an angle sensor in the image capture system.

3. The method of claim 1, wherein the tilt detection system detects a tilt angle along one axis or along multiple axes.

4. The method of claim 1, further comprising: displaying a number of degrees for the user to rotate the image capture system.

5. The method of claim 1, further comprising: providing a color change on the display screen when the image capture system is rotated from an unacceptable tilt angle relative to horizontal to an acceptable tilt angle relative to horizontal.

6. The method of claim 1, further comprising: automatically triggering autofocus and image capture when the tilt angle is within an acceptable range.

7. The method of claim 1, further comprising: providing haptic feedback to notify the user that the image capture process started.

8. The method of claim 1, further comprising: providing a blur detection artificial intelligence mechanism that determines when there is an unacceptable amount of blurriness in an image of the rapid test device, wherein the blur detection artificial intelligence mechanism uses a machine learning classification system to train on distinguishing blurry images from non-blurring images.

9. The method of claim 1, further comprising: tracking, via multiple timers, concurrent test results.

10. The method of claim 1, wherein presenting a quantitative level of the result further comprises: presenting an indication of a negative result, a low positive result, a medium positive result, or a strong positive result.

11. A rapid-test-validation computing device, comprising:
an image capture system with a display screen;
a tilt detection system with an accelerometer and an angle sensor;
a memory that stores computer instructions; and
a processor that executes the computer instructions to:
obtain one or more first images of a rapid test device using the image capture system with a display screen;
present the one or more images to a user on the display screen with alignment bars as the one or more first images are being captured;
determine a position of the rapid test device in the one or more first images relative to the alignment bars;
in responsive to determining that the position of the rapid test device relative to the alignment bars is not in an acceptable range, prompt the user of the image capture system to reposition the image capture system with respect to the alignment bars;
determine, via a tilt detection system, a tilt angle of the image capture system with respect to horizontal;
in responsive to determining that the tilt angle of the image capture system relative to horizontal is not in an acceptable range, prompt the user of the image capture system to rotate the image capture system relative to horizontal;
responsive to the position of the rapid test device being in an acceptable range relative to the alignment bars in at least one of the one or more first images, and responsive to the tilt angle of the image capture system being in an acceptable range relative to horizontal:
    capture one or more second images of the rapid test device;
    determine when a result of the rapid test device is valid;
    present an invalid-test-result notification to the user when the result of the rapid test device is invalid; and
    determine a quantitative level of the result of the rapid test device when the result of the rapid test device is valid.

12. The device of claim 11, further comprising: initiating instructions to present the quantitative level of the result.

13. The device of claim 11, wherein the tilt detection system uses a accelerometer and an angle sensor in the image capture system.

14. The device of claim 11, wherein the tilt detection system detects a tilt angle along one axis or along multiple axes.

15. The device of claim 11, further comprising: displaying an actual number of degrees for the user to rotate the image capture system.

16. The device of claim 11, further comprising: providing a color change when the image capture system is rotated from an unacceptable tilt angle relative to horizontal to an acceptable tilt angle relative to horizontal.

17. The device of claim 11, further comprising: automatically triggering autofocus and image capture when the tilt angle is within an acceptable range.

18. The device of claim 11, further comprising: providing haptic feedback to notify the user that the image capture process started.

19. The device of claim 11, further comprising: providing a blur detection artificial intelligence mechanism that determines when there is an unacceptable amount of blurriness in an image of the rapid test device, wherein the blur detection artificial intelligence mechanism uses a machine learning classification system to train on distinguishing blurry images from non-blurring images.

20. The device of claim 11, in response to the blur detection artificial intelligence mechanism determining there is an un-acceptable amount of blurriness in the image of the rapid test device, initiating capture of a replacement image.

21. The device of claim 11, wherein the rapid test results imaging device includes multiple timers for tracking concurrent test results.

22. The device of claim 11, wherein presenting a quantitative level of the results further comprises: presenting an indication of a negative result, a low positive result, a medium positive result, or a strong positive result.

23. A rapid test results imaging method for determining the intensity of a test line, the method comprising:
    capturing one or more first images of a lateral flow assay cassette using an image capture system with a display screen;
    presenting the one or more images to a user on the display screen with alignment bars as the one or more first images are being captured;
    determining a position of the lateral flow assay cassette in the one or more first images relative to the alignment bars;
    in responsive to determining that the position of the rapid test device relative to the alignment bars is not in an acceptable range, prompting the user of the image capture system to reposition the image capture system with respect to the alignment bars;
    determining, via a tilt detection system, a tilt angle of the image capture system with respect to horizontal;
    in responsive to determining that the tilt angle of the image capture system relative to horizontal is not in an acceptable range, prompting the user of the image capture system to rotate the image capture system relative to horizontal;
    responsive to the position of the lateral flow assay cassette being in an acceptable range relative to the alignment bars in at least one of the one or more first images, and responsive to the tilt angle of the image capture system being in an acceptable range relative to horizontal:
        capturing one or more second images of the lateral flow assay cassette;
        determining when a result of the lateral flow assay cassette is valid;
        responsive to the result of the lateral flow assay cassette being invalid, presenting an invalid-test-result notification to the user;
        responsive to the result of the lateral flow assay cassette being valid, determining a presence of a quantitative amount of a neutralizing antibody in the lateral flow assay cassette; and
        presenting the presence of the quantitative amount of neutralizing antibody to the user.

24. The method of claim 23, further comprising:
    determining the intensity of a control line by analytical methods comprising integrating grayscale images around the control line and determining a peak value present in the control line;
    determining the intensity of the test line by analytical methods comprising integrating grayscale images around the test line and determining the peak value present in the test line;
    determining a ratio of the test line peak value to the control line peak value; and
    using the determined ratio to present the presence of quantitative amount of neutralizing antibody in the result to the user.

\* \* \* \* \*